United States Patent [19]

Clitherow et al.

[11] Patent Number: 4,670,448
[45] Date of Patent: Jun. 2, 1987

[54] TRIAZOLE AMINE COMPOUNDS, THEIR PHARMACEUTICAL COMPOSITIONS AND METHOD OF USE

[75] Inventors: John W. Clitherow; John Bradshaw; John W. M. Mackinnon; Duncan B. Judd; David E. Bays; Roger Hayes; Andrew Pearce, all of Hertfordshire, United Kingdom

[73] Assignee: Glaxo Group Limited, London, England

[21] Appl. No.: 465,616

[22] Filed: Feb. 10, 1983

Related U.S. Application Data

[63] Continuation of Ser. No. 238,688, Feb. 27, 1981, abandoned.

[30] Foreign Application Priority Data

Feb. 28, 1980 [GB] United Kingdom ............... 8006806

[51] Int. Cl.$^4$ .................. C07D 401/12; A61K 31/41
[52] U.S. Cl. .................................. 514/334; 514/340; 514/383; 514/384; 546/210; 546/276; 548/161; 548/212; 548/233; 548/245; 548/252; 548/253; 548/254; 548/266

[58] Field of Search ............... 546/210, 276; 548/161, 548/212, 233, 245, 252, 253, 254, 266; 424/267, 269, 263, 270, 272

[56] References Cited

FOREIGN PATENT DOCUMENTS 1419994  1/1976  United Kingdom .
2003471  3/1979  United Kingdom ............... 546/210
2023133 12/1979  United Kingdom .

Primary Examiner—Robert T. Bond
Attorney, Agent, or Firm—Bacon & Thomas

[57] ABSTRACT

The invention provides compounds of the general formula (I)

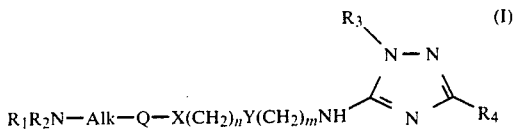

and physiologically acceptable salts, hydrates and bioprecursors thereof, in which the substituents are defined in the detailed description.

The compounds show pharmaceutical activity as selective histamine $H_2$-antagonists.

19 Claims, No Drawings

TRIAZOLE AMINE COMPOUNDS, THEIR PHARMACEUTICAL COMPOSITIONS AND METHOD OF USE

This application is a continuation of application Ser. No. 238,688, filed Feb. 27, 1981, now abandoned.

This invention relates to novel heterocyclic derivatives having action on histamine receptors, to processes for the preparation thereof, to pharmaceutical compositions containing them and to their use in therapeutics.

Certain novel heterocyclic derivatives have now been found which have potent activity as $H_2$-antagonists. These compounds, which are more particularly described below, for example show inhibition of the secretion of gastric acid when this is stimulated via histamine receptors (Ash and Schild, Brit. J. Pharmacol. Chemother, 1966, 27, 427). Their ability to do so can be demonstrated in the perfused rat stomach using the method described in German Offenlegungsschrift No. 2,734,070, modified by the use of sodium pentobarbitone (50 mg/kg) as anaesthetic instead of urethane, and in conscious dogs equipped with Heidenhain pouches using the method described by Black et al, Nature 1972 236, 385. Furthermore the compounds antagonise the effect of histamine on the contraction frequency of isolated guinea pig right atrium but do not modify histamine induced contractions of isolated gastrointestinal smooth muscle which are mediated via $H_1$-receptors.

Compounds with histamine $H_2$-blocking activity may be used in the treatment of conditions where there is an advantage in lowering gastric acidity, particularly in gastric and peptic ulceration, as a prophylactic measure in surgical procedures, and in the treatment of allergic and inflammatory conditions where histamine is a known mediator. Thus they may be used for example, either alone or in combination with other active ingredients in the treatment of allergic and inflammatory conditions of the skin.

The present invention provides compounds of the general formula (I)

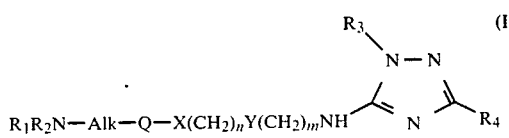

and physiologically acceptable salts, hydrates and bioprecursors thereof, in which $R_1$ represents hydrogen, $C_{1-14}$ alkyl, cycloalkyl, alkenyl, alkynyl, aralkyl, heteroaralkyl, trifluoroalkyl or alkyl substituted by hydroxy, alkoxy, amino, alkylamino, dialkylamino or cycloalkyl; and $R_2$ represents hydrogen or $C_{1-4}$ alkyl; or $R_1$ and $R_2$ may together with the nitrogen atom to which they are attached form a 5 to 10 membered ring which may be saturated or may contain at least one double bond, may be unsubstituted or may be substituted by one or more $C_{1-3}$ alkyl e.g. methyl, groups or a hydroxy group and/or may contain another heteroatom e.g. oxygen or sulphur.

Alk represents a straight or branched alkylene chain of 1 to 6 carbon atoms,

Q represents a furan or thiophen ring in which incorporation into the rest of the molecule is through bonds at the 2- and 5-positions, the furan or thiophen ring optionally bearing a further substituent $R_5$ adjacent to the group $R_1R_2N$—Alk—; or Q represents a thiophen ring in which incorporation into the rest of the molecule is through bonds at the 2- and 4-positions, the thiophen ring optionally bearing a further substituent $R_5$ adjacent to the group $R_1R_2NAlk$ with the proviso that when the group $R_1R_2NAlk$ is in the 4-position then the group $R_5$ is in the 5-position; or Q represents a benzene ring in which incorporation into the rest of the molecule is through bonds at the 1- and 3- or 1- and 4-positions;

$R_5$ represents halogen or $C_{1-4}$ alkyl which may be substituted by hydroxy or $C_{1-4}$ alkoxy;

X represents oxygen, sulphur, —NH—, methylene or a bond;

Y represents oxygen, sulphur, methylene or a bond;

n represents zero, 1, 2 or 3, and m is an integer from 2 to 5, with the provisos that (a) the total number of atoms in the chain $X(CH_2)_nY(CH_2)_m$ is an integer from 3 to 8, when X and Y represent oxygen or sulphur then n is 2 or 3, and (c) when X represents —NH— then Q is a benzene ring and Y represents methylene or a bond;

$R_3$ represents hydrogen, alkyl, alkenyl, aralkyl, or $C_{2-6}$ alkyl substituted by hydroxy or alkoxy;

$R_4$ represents the group $(CH_2)_pCH=CHR_6$ or $(CH_2)_qR_7$ where p is zero, 1, or 2 and q is zero, 1,2, 3, 4, 5 or 6 and the alkylene chain $(CH_2)_q$ may be straight or branched, and $R_6$ is hydroxymethyl, 1H-tetrazol-5-yl, cyano, or the group $CH_2NHCOR_{17}$ or $CH_2NHSO_2R_{17}$ is alkyl; or the group $COR_{19}$ where $R_{19}$ is hydrogen, hydroxyl, alkyl, alkoxy, amino, alkylamino or dialkylamino, or the group $CR^a{}_{19}=NR_{20}$ where $R^a{}_{19}$ is hydrogen or alkyl and $R_{20}$ is hydroxy, alkoxy, aralkyloxy or —NHC(=A)NH_2$ where A is oxygen or sulphur;

$R_7$ is nitro, cyano, halomethyl, heteroaryl, arylaminomethyl, aralkylaminomethyl, alkylthioalkyl, arylthioalkyl, 1H-tetrazol-5-yl, aryl $CH=NCH_2$—or $CH_2NHC(=B)NHR_{17}$ where B is NCN, $NSO_2$Methyl, $NSO_2$Phenyl or $CHNO_2$;

or $R_7$ is the group $SO_2R_8$ in which $R_8$ is hydroxy, alkyl, aryl or the group $NR_9R_{10}$ where $R_9$ and $R_{10}$ are the same or different and represent hydrogen, alkyl, aryl or aralkyl;

or $R_7$ is the group $COR_{11}$ where $R_{11}$ is hydrogen, hydroxy, alkoxy, aryloxy, aralkyloxy, alkyl, aryl, aralkyl or the group $NR_{12}R_{13}$ where $R_{12}$ is hydrogen or alkyl optionally substituted by a hydroxy or alkoxy group, and $R_{13}$ is hydrogen, alkyl (optionally substituted by a hydroxy or alkoxy group), alkenyl, aryl, aralkyl or cycloalkyl, or $NR_{12}R_{13}$ forms a 5 to 8 membered ring which may contain another heteroatom e.g. oxygen, or a double bond and/or may be substituted by hydroxy or one or two $C_{1-3}$ alkyl (e.g. methyl) groups;

or $R_7$ is the group $CR^a{}_{11}=NR_{20}$ where $R^a{}_{11}$ is hydrogen, alkyl, aryl or arlkyl and $R_{20}$ is as defined above;

or $R_7$ is the group $CH_2NR_{18}SO_2R_{14}$ where $R_{14}$ alkyl or aryl and $R_{18}$ is hydrogen or alkyl;

or $R_7$ is the group $CH_2NR_{18}COR_{15}$ where $R_{15}$ is hydrogen, alkyl, aryl, aralkyl, alkoxy, halomethyl, or the group $NHR_{16}$ where $R_{16}$ is hydrogen, alkyl, cycloalkyl, aryl or aralkyl;

with the proviso that when the group $R_7$ contains a carbon atom through which it is linked to the alkylene group $(CH_2)_q$ then the total number of carbon atoms in the resulting chain is not greater than 6 (i.e. q is not greater than 5).

The term "alkyl" as a group or a part of a group means that the group is straight or branched and, unless otherwise stated, has preferably 1 to 6 carbon atoms, and in particular 1 to 4 carbon atoms, e.g. methyl or ethyl, and the terms "alkenyl" and "alkynyl" mean that the group has preferably 3 to 6 carbon atoms. The term "cycloalkyl" means that the group 3 to 8 carbon atoms. The term "halomethyl" means a mono-, di- or trihalo substituted methyl group, e.g. monochloro or trifluoro. The term "aryl" as a group or part of a group preferably means phenyl or substituted phenyl, for example phenyl substituted with one or more $C_{1-3}$ alkyl or alkoxy groups, or halogen atoms e.g. fluorine. The term "heteroaryl" as a group or part of a group means a 5 or 6 membered monocyclic ring containing 1 to 3 heteroatoms selected from oxygen, nitrogen and sulphur, e.g. thienyl, pyridyl, furyl or thiazolyl. The heteroaryl ring may be unsubstituted or substituted by $C_{1-3}$ alkyl, $C_{1-3}$ alkoxy, hydroxy, hydroxyalkyl, aminoalkyl, alkylaminoalkyl, dialkylaminoalkyl or halogen. The alkyl portion of a heteroaralkyl group is a straight or branched $C_{1-4}$ alkyl chain, and the heteroaryl ring is linked to the alkyl portion through either a carbon or nitrogen atom.

In the compounds according to the invention preferably $R_1$ represents $C_{1-12}$ alkyl (e.g. methyl, ethyl, propyl, butyl, isobutyl, hexyl, heptyl or undecyl), $C_{5-7}$ cycloalkyl (e.g. cyclohexyl), $C_{3-5}$ alkenyl (e.g. allyl or 3,3-dimethylallyl), phenyl $C_{1-3}$ alkyl (e.g. benzyl), $C_{1-4}$ alkyl substituted by a trifluoromethyl, hydroxy, $C_{1-3}$ alkoxy or di-$C_{1-3}$ alkylamino group (e.g. 2,2,2-trifluoroethyl, 3-hydroxypropyl, methoxyethyl, ethoxyethyl, dimethylaminoethyl, diethylaminoethyl or dimethylaminopropyl) or a heteroaryl $C_{1-3}$ alkyl group where the heteroaryl ring contains one heteroatom (e.g. furylmethyl, pyridylmethyl, thienylmethyl, pyrrolylmethyl, (5-methylfuran-2-yl)methyl or (5-hydroxymethylfuran-2-yl)methyl; and $R_2$ represents hydrogen, methyl or ethyl; or $R_1R_2N$ represents a 5 to 8 membered ring optionally containing one double bond and/or substituted by one or two $C_{1-3}$ alkyl (e.g. methyl) groups (e.g. pyrrolidino, piperidino, hexamethylenimino, tetrahydropyridino, 4-hydroxypiperidino or 4-methylpiperidino).

More preferably $R_1R_2N$ represents $C_{1-8}$ alkylamino (e.g. hexylamino), di-$C_{1-2}$ alkylamino (e.g. dimethylamino), furylmethylamino or a saturated 5-7 membered ring (e.g. piperidino).

$R_3$ preferably represents hydrogen, $C_{1-4}$ alkyl (e.g. methyl, ethyl, or propyl), or hydroxy $C_{2-4}$ alkyl (e.g. 2-hydroxyethyl); more preferably hydrogen or $C_{1-3}$ alkyl (e.g. methyl).

Within the definition of $R_4$, p is preferably zero and $R_6$ is preferably hydroxymethyl or the group $COR_{19}$ where $R_{19}$ is hydroxy, amino, $C_{1-4}$ alkylamino or di-$C_{1-4}$ alkylamino; more preferably $R_6$ is hydroxymethyl or $COR_{19}$ where $R_{19}$ is hydroxy.

q is preferably zero, 1, 2 or 3; and $R_7$ is preferably nitro, cyano, halomethyl (e.g. chloromethyl or trifluoromethyl), heteroaryl (e.g. pyridyl or thienyl), alkylthioalkyl (e.g. methylthiomethyl), 1H-tetrazol-5-yl, —$CH_2NHC(=B)NHR_{17}$ where B is NCN or $CHNO_2$ and $R_{17}$ is alkyl (e.g. methyl), or the group $SO_2R_8$ where $R_8$ is hydroxy, alkyl e.g. (methyl), or aryl (e.g. phenyl); or the group $COR_{11}$ where $R_{11}$ is hydrogen, hydroxy, alkoxy (e.g. ethoxy), alkyl (e.g. methyl) or the group $NR_{12}R_{13}$ where $R_{12}$ and/or $R_{13}$ are hydrogen or alkyl (e.g. methyl), or $NR_{12}R_{13}$ forms a 5- or 6-membered ring (e.g. pyrrolidino); or the group $CH=NR_{20}$ where $R_{20}$ is hydroxy or alkoxy (e.g. methoxy), or $R_7$ is the group $CH_2NHSO_2R_{14}$ or $CH_2NHCOR_{15}$ where $R_{14}$ is alkyl (e.g. methyl), and $R_{15}$ is alkyl (e.g. methyl), aryl (e.g. phenyl), arylamino (e.g. phenylamino) or halomethyl (e.g. trifluoromethyl).

More preferably $R_4$ represents nitro, alkylthiomethyl (e.g. methylthiomethyl), heteroarylmethyl (e.g. pyridylmethyl), $CH=NR_{20}$ where $R_{20}$ is hydroxy; or the group $(CH_2)_qR_7$ where q is zero, 1 or 2, and $R_7$ is the group $CH_2NHC(=B)NHR_{17}$ where B is NCN or $CHNO_2$ and $R_{17}$ is alkyl (e.g. methyl); or $R_7$ is the group $COR_{11}$ where $R_{11}$ is hydrogen, hydroxy or $NR_{12}R_{13}$ where $R_{12}$ and/or $R_{13}$ are hydrogen or alkyl (e.g. methyl), or $NR_{12}R_{13}$ forms a 5- or 6-membered ring (e.g. pyrrolidino); or $R_7$ is the group $SO_2R_8$ where $R_8$ is alkyl (e.g. methyl) or aryl (e.g. phenyl); or $R_7$ is the group $CH_2NHSO_2R_{14}$ or $CH_2NHCOR_{15}$ where $R_{14}$ is alkyl (e.g. methyl), and $R_{15}$ is alkyl (e.g. methyl), aryl (e.g. phenyl) or $NHR_{16}$ where $R_{16}$ is aryl (e.g. phenyl).

When Q represents a thiophen ring containing a further substituent $R_5$, $R_5$ is preferably bromine, $C_{1-3}$ alkyl (e.g. methyl, ethyl or isopropyl), $C_{1-3}$ alkoxy $C_{1-3}$ alkyl (e.g. methoxymethyl), or hydroxy $C_{1-3}$ alkyl (e.g. hydroxymethyl); more preferably methyl.

The group Alk preferably contains 1-4 carbon atoms and may be for example a methylene, ethylene or propylene group. More preferably Alk represents methylene.

The chain $X(CH_2)_nY(CH_2)_m$ preferably contains from 4 to 6 atoms. More particularly when Q is benzene the group $X(CH_2)_nY(CH_2)_m$ preferably represents —$O(CH_2)_{3-5}$— or —$O(CH_2)_2O(CH_2)_2$—, more preferably —$O(CH_2)_{3-4}$—. When Q is an optionally substituted furan or thiophene ring the group $X(CH_2)_nY(CH_2)_m$ is preferably —$CH_2S(CH_2)_2$—, —$CH_2O(CH_2)_3$— or $(CH_2)_4$—, more preferably —$CH_2S(CH_2)_2$—. Most preferably Q is a benzene ring incorporated into the rest of the molecule through bonds at the 1- and 3-positions.

A preferred group of compounds are those of the formula (IA)

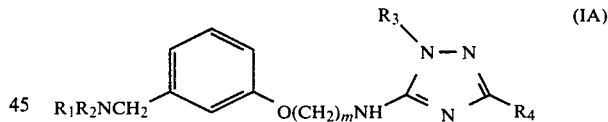

where $R_1R_2N$ is pyrrolidino, piperidino or hexamethylenimino (preferably piperidino); m is 3 or 4; $R_3$ is hydrogen or methyl; and $R_4$ is the group $(CH_2)_qR_7$ where q is zero, 1 or 2, and $R_7$ is methylthiomethyl, $CH_2NHC(=B)NHCH_3$ (where B is NCN or $CHNO_2$), $SO_2Me$, $CH=NOH$; or the group $COR_{11}$ where $R_{11}$ is hydroxy, amino, dimethylamino or pyrrolidino; or the group $CH_2NHSO_2Me$; or the group $CH_2NHCOR_{15}$ where $R_{15}$ is methyl or phenyl. Within this group of compounds, when q is zero, $R_{11}$ is preferably other than amino.

Particularly preferred compounds are:

N-[[1-Methyl-5-[[3-[3-(1-piperidinylmethyl)phenoxy]propyl]amino]-1H-1,2,4-triazol-3-yl]methyl]methanesulphonamide.

1-Methyl-3-methylsulphonylmethyl-N-[3-[3-(1-piperidinylmethyl)phenoxy]propyl]-1H-1,2,4-triazole-5-amine.

N-[[1-Methyl-5-[[3-[3-(1-piperidinylmethyl)phenoxy]propyl]amino]-1H-1,2,4-triazol-3-yl]methyl]acetamide.

1-Methyl-5-[[3-[3-(1-piperidinylmethyl)phenoxy]-propyl]amino]-1H-1,2,4-triazole-3-carboxamide.

N-[[1-Methyl-5-[[3-[3-(1-piperidinylmethyl)phenoxy]-propyl]amino]-1H-1,2,4-triazol-3-yl]methyl]benzamide.

5-[4-[3-(1-Piperidinylmethyl)phenoxy]butyl]amino-1H-1,2,4-triazole-3-carboxamide.

1-Methyl-5-[[3-[3-(1-piperidinylmethyl)phenoxy]-propyl]amino]-1H-1,2,4-triazole-3-carboxylic acid.

1-Methyl-3-methylthiomethyl-N-[3-[3-(1-piperidinylmethyl)phenoxy]propyl]-1H-1,2,4-triazole-5-amine.

3-Methylsulphonyl-N-[4-[3-(1-piperidinylmethyl)-phenoxy]butyl]-1H-1,2,4-triazole-5-amine.

1-Methyl-5-[[3-[3-(1-piperidinylmethyl)phenoxy]-propyl]amino]-1H-1,2,4-triazole-3-acetic acid.

N-Methyl-N'-[[1-methyl-5-[[3-[3-(1-piperidinylmethyl)-phenoxy]propyl]amino]-1H-1,2,4-triazol- 3-yl]methyl]-2-nitro-1,1-ethenediamine.

N,N,1-Trimethyl-5-[[3-[3-(1-piperidinyl)methyl]-phenoxy]propyl]amino-1H-1,2,4-triazole-3-propanamide.

1-[3-[1-methyl-5-[[3-[3-(1-piperidinylmethyl)phenoxy]-propyl]amino]-1H-1,2,4-triazol-3-yl]-1-oxopropyl]-pyrrolidine.

1-Methyl-5-[[3-[3-(1-piperidinylmethyl)phenoxy]-propyl]amino]-1H-1,2,4-triazole-3-carboxaldehyde oxime.

N-[3-[1-methyl-5-[[3-[3-(1-piperidinylmethyl)phenoxy]-propyl]amino]-1H-1,2,4-triazol-3-yl]propyl]methanesulphonamide.

N-Cyano-N'-methyl-N''-[[1-methyl-5-[[3-[3-(1-piperidinylmethyl)phenoxy]propyl]amino]-1H-1,2,4-triazol-3-yl]methyl]guanidine and their physiologically acceptable salts.

According to one aspect the invention provides compounds of formula (I) in which $R_1$ represents hydrogen, $C_{1-10}$ alkyl, cycloalkyl, alkenyl, alkynyl, aralkyl, trifluoroalkyl, or alkyl substituted by hydroxy, alkoxy, amino, alkylamino, dialkylamino or cycloalkyl; and $R_2$ represents hydrogen or $C_{1-4}$ alkyl; or $R_1$ and $R_2$ may together with the nitrogen atom to which they are attached form a 5 to 10 membered ring which may be saturated or may contain at least one double bond, may be unsubstituted or may be substituted by one or more $C_{1-3}$ alkyl groups or a hydroxy group and/or may contain another heteroatom;

Alk represents a straight or branched alkylene chain of 1 to 6 carbon atoms;

Q represents a furan or thiophen ring in which incorporation into the rest of the molecule is through bonds at the 2- and 5-positions, the furan ring optionally bearing a further substituent $R_5$ adjacent to the group $R_1R_2N$-Alk; or Q represents a benzene ring in which incorporation into the rest of the molecule is through bonds at the 1- and 3- or 1- and 4- positions;

$R_5$ represents halogen or $C_{1-4}$ alkyl which may be substituted by hydroxy or $C_{1-4}$ alkoxy;

X represents a bond or, when Q is a benzene ring and Y is methylene or a bond, —NH—;

Y represents oxygen, sulphur or methylene;

n represents zero, 1 or 2;

m represents 2, 3 or 4;

$R_3$ represents hydrogen, alkyl, alkenyl, aralkyl, or $C_{2-6}$ alkyl substituted by hydroxy or alkoxy; and $R_4$ represents the group $(CH_2)_qR_7$ where q is zero, 1, 2, 3, 4, 5 or 6 and the alkylene chain $(CH_2)_q$ may be straight or branched, and $R_7$ is nitro, halomethyl, heteroaryl, arylaminomethyl, aralkylaminomethyl, or Aryl $CH=NCH_2—$;

or $R_7$ is the group $SO_2R_8$ in which $R_8$ is alkyl, aryl or the group $NR_9R_{10}$ where $R_9$ and $R_{10}$ are the same or different and represent hydrogen, alkyl, aryl or aralkyl;

or $R_7$ is the group $COR_{11}$ where $R_{11}$ is hydrogen, hydroxy, alkoxy, aryloxy, aralkyloxy, alkyl, aryl, aralkyl or the group $NR_{12}R_{13}$ where $R_{12}$ is hydrogen or alkyl optionally substituted by a hydroxy or alkoxy group, and $R_{13}$ is hydrogen, alkyl optionally substituted by a hydroxy or alkoxy group, alkenyl, aryl, aralkyl or cycloalkyl, or $NR_{12}R_{13}$ forms a 5 to 8 membered ring which may contain another heteroatom, or a double bond and/or may be substituted by hydroxy or one or two $C_{1-3}$ alky groups;

or $R_7$ is the group $CR^a{}_{11}=MR_{20}$ where $R^a{}_{11}$ is hydrogen, alkyl, aryl o. aralkyl, and $R_{20}$ is hydroxy, alkoxy or —NHC(=A)NH$_2$ where A is oxygen or sulphur.

or $R_7$ is the group $CH_2NR_{18}SO_2R_{14}$ where $R_{14}$ is alkyl or aryl and $R_{18}$ is hydrogen or alkyl;

or $R_7$ is the group $CH_2NR_{18}COR_{15}$ where $R_{15}$ is hydrogen, alkyl, aryl, aralkyl, alkoxy or the group $NHR_{16}$ where $R_{16}$ is hydrogen, alkyl, cycloalkyl, aryl or aralkyl;

With the proviso that when the group $R_7$ contains a carbon atom through which it is linked to the alkylene group $(CH_2)_q$ then the total number of carbon atoms in the resulting chain is not greater than 6 (i.e., q is not greater than 5). Preferably when q is zero, $R_7$ does not represent heteroaryl or $COR_{11}$ where $R_{11}$ is alkoxy or $NR_{12}R_{13}$ where $R_{12}$ and $R_{13}$ are both hydrogen.

According to a further aspect the invention provides compounds of formula (I) in which $R_4$ represents $(CH_2)_qR_7$ where $R_7$ is —$CH_2NHC(=B)NH$ $R_{17}$.

According to another aspect the invention provides compounds of formula (I) in which $R_4$ represents $(CH_2)_pCH=CHR_6$ wherein $R_6$ and p are as defined above or $R_4$ represents $(CH_2)_qR_7$ where q is zero, 1, 2, 3, 4, 5 or 6 and the alkylene chain may be straight or branched and $R_7$ is alkylthioalkyl, arylthioalkyl, 1H-tetrazol-5-yl, or $R_7$ is the group $SO_2R_8$ where $R_8$ is hydroxy, or $R_7$ is the group $CH_2NR_{18}COR_{15}$ where $R_{15}$ is halomethyl.

The invention includes the compounds of formula (I) in the form of physiologically acceptable salts with inorganic and organic acids. Particularly useful salts include hydrochlorides, hydrobromides, sulphates, methanesulphonates, acetates, maleates, succinates, citrates, tartrates, fumarates and benzoates. The compounds of formula (I) and their salts may also form hydrates, which hydrates are also to be considered as part of the invention. The compounds of formula (I) can exhibit tautomerism and the formula is intended to cover all tautomers. Where optical isomers may exist the formula is intended to cover all diastereoisomers and optical enatiomers. The term bioprecursors as used herein means compounds which have a structure different to that of the compunds of formula (I) but which, upon administration to the animal or human being, are converted in the body into a compound of formula (I).

The compounds according to the invention, preferably in the form of a salt, may be formulated for administration in any convenient way and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients e.g. $H_1$-antagonists.

Thus the compounds according to the invention may be formulated for oral, buccal, topical, parenteral or rectal administration. Oral administration is preferred.

For oral administration, the pharmaceutical composition may take the form of for example, tablets, capsules, powders, solutions, syrups or suspensions prepared by conventional means with acceptable excipients. For buccal administration the composition may take the form of tablets or lozenges formulated in conventional manner.

The compounds of the invention may be formulated for parenteral administration by bolus injection or continuous infusion. Formulations for injection may be present in unit dosage form in ampoules, or in multidose containers, with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form for reconstitution with a soluble vehicle e.g. sterile pyrogen-free water before use.

The compounds of the invention may also be formulated in rectal compositions such as suppositories or retention enemas, e.g. containing conventional suppository bases such as cocoa butter or other glycerides.

For topical application, the compounds of the invention may be formulated as ointments, creams, gels, lotions, powders or sprays in a conventional manner.

For internal administration a convenient daily dosage regime of the compounds according to the invention would be 1 to 4 doses to the total of some 5 mg. to 1 g per day, preferably 5 to 250 mg. per day, dependent upon the condition of the patient.

It wil be appreciated that in the methods for the preparation of compounds of formula (I) given below, for certain reaction steps it may be necessary to protect various reactive substituents in the starting materials for a particular reaction and subsequently to remove the protecting group. Such protection and subsequent deprotection may be particularly pertinent where $R_1$ and $R_2$ in intermediates used to prepare compounds of formula (I) are hydrogen atoms and/or when $R_3$ in intermediates is an alkyl group bearing a hydroxy substituent and/or when $R_4$ contains an amino group. Standard protection and deprotection procedures can be employed, for example amines may be protected by formation of a phthalimide group which may subsequently be cleaved by treatment with a hydrazine, e.g. hydrazine hydrate or a primary amine, for example methylamine.

In describing the processes which may be used for preparing the compounds of formula (I) or intermediates useful in the preparation thereof, any of $R_1$ to $R_{20}$, A, B, Alk, Q, X, Y, n, m, p and q in the various formulae are as defined in formula (1) unless otherwise stated.

Compounds of formula (I) in which $R_7$ is the group $CH_2NR_{18}COR_{15}$, $CH_2NR_{18}SO_2R_{14}$, $CH_2NHC(=B)NHR_{17}$ or $-CH_2N=CH$ Aryl, or $R_6$ is the group $CH_2NHCOR_{17}$ or $CH_2NHSO_2R_{17}$ may be prepared by treating an aminoalkyltriazole of formula (II)

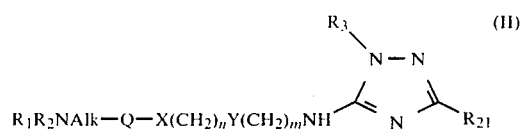

in which $R_1$, $R_2$ and $R_3$ are as defined in formula (I) or are groups readily convertible thereto, and $R_{21}$ is the group $(CH_2)_{q+1}NHR_{18}$ or the group $(CH_2)_pCH=CHCH_2NH_2$, with a compound capable of replacing the hydrogen atom in the group $NHR_{18}$ by the group $COR_{15}$, $SO_2R_{14}$ or $C(=B)NHR_{17}$, or the hydrogen atom in the group $NH_2$ by the group $COR_{17}$ or $SO_2R_{17}$, or both hydrogen atoms in the group $NHR_{18}$ where $R_{18}$ is hydrogen by $=CH$ Aryl.

Thus for example the aminoalkyltriazole (II) in which $R_{21}$ is the group $(CH_2)_{q+1}NHR_{18}$ may b reacted with an isocyanate $R_{16}'NCO$ in which $R'_{16}$ has any of the meanings defined for $R_{16}$ in formula (I) except hydrogen or represents an alkali metal atom such as potassium or sodium, or with an activated derivative of either a carboxylic acid $R_{15}COOH$ (in which $R_{15}$ is other than the group $NHR_{16}$) or a sulphonic acid $R_{14}SO_3H$ to give a compound of formula (I) in which $R_7$ is respectively the group $CH_2NR_{18}CONHR_{16}$, $CH_2NR_{18}COR_{15}$ (in which $R_{15}$ is other than $NHR_{16}$), or $CH_2NR_{18}SO_2R_{14}$. Similarly an aminoalkyltriazole (II) in which $R_{21}$ is the group $(CH_2)_pCH=CHCH_2NH_2$ may be treated with an activated derivative of either a carboxylic acid $R_{17}COOH$ or a sulphonic acid $R_{17}SO_3H$ to give a compound of formula (I) in which $R_6$ is respectively the group $CH_2NHCOR_{17}$ or $CH_2NHSO_2R_{17}$.

Suitable activated derivatives include acid halides e.g. acid chlorides, alkylchlorformates, acid anhydrides including mixed anhydrides (e.g. acetic formic anhydride), esters such as alkyl esters, ortho esters and (1-alkyl-2-pyridinyl)esters, or derivatives formed from a coupling agent such as carbonyldiimidazole or a carbodiimide such as dicyclohexylcarbodiimide.

The reaction with an acid halide is preferably carried out in the presence of a base e.g. an inorganic base such as sodium hydroxide or an organic base such as triethylamine or pyridine. The reaction with an alkylchloroformate is preferably carried out in the presence of a base, e.g. potassium carbonate or triethylamine, in a solvent such as dimethylformamide. The reaction with an acid anhydride may be carried out in the absence of presence of solvent such as pyridine.

In the reaction with an isocyanate compounds of formula (I) in which $R_{16}$ is other than hydrogen are conveniently prepared by carrying out the reaction in a solvent such as acetonitrile at temperatures from ambient to reflux. Compounds of formula (I) in which $R_{16}$ is hydrogen may be prepared by heating a salt e.g. hydrochloride of the aminotriazole (II) with an aqueous solution of an appropriate cyanate eg. potassium cyanate.

As a further embodiment of this process an aminoalkyltriazole (II) in which $R_{21}$ is the group $(CH_2)_{q+1}NHR_{18}$ where $R_{18}$ is hydrogen may be treated with a compound of formula $LC(=B)NHR_{17}$ where L is a leaving group (e.g. methylthio) to give a compound of formula (I) in which $R_7$ is $CH_2NHC(=B)NHR_{17}$. The reactants may for example be mixed in an aqueous solution at room temperature.

In yet another embodiment of this process an aminoalkyltriazole (II) in which $R_{21}$ is the group $(CH_2)_{q+1}NHR_{18}$ where $R_{18}$ is hydrogen is treated with an appropriate aromatic aldehyde, e.g. benzaldehyde to give a product in which $R_7$ is $CH_2N=CH$ Aryl.

Aminoalkyltriazoles of formula (II) may be prepared by method described in or analogous to those described in British Patent Specification No. 2047238A.

In an alternative method for preparing compounds of formula (I) in which $R_7$ is the group $CH_2NHC(=B)NHR_{17}$, a diamine of formula (II) in which $R_{21}$ is the group $(CH_2)_{q+1}NH_2$ may be with a compound of formula $LC(=B)L$ in which L is a leaving group (e.g. methylthio), followed by reaction with an appropriate alkylamine $R_{17}NH_2$. The diamine ((II) in which $R_{21}$ is the group $(CH_2)_{q+1}NH_2$ may be treated with the compound of formula $LC(=B)L$ in a suitable solvent (e.g. diethyl ether) optionally with heating and the reaction with the amine $R_{17}NH_2$ may be carried out in a solvent such as ethanol again optionally with heating.

Compounds of formula (I) in which $R_4$ is other than nitro, cyano, mono- or dihaloalkyl, 1H-tetrazol-5-yl, the group $SO_2R_8$, the group $COR_{11}$ where $R_{11}$ is hydrogen, alkyl, aryl or aralkyl, or the group $CR^a{}_{11}=NR_{20}$ may be prepared by cyclisation of a compound of formula (IV)

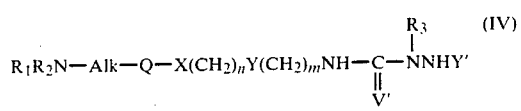

in which V' is

and Y' is hydrogen where V is oxygen or sulphur and R'$_4$ is a group as defined for $R_4$ above or a group convertible thereto under the conditions of the cyclisation reaction or V' is NH and Y' is

where Y'' is sulphur, oxygen or NH; or V' is sulphur or oxygen and Y' is

Thus for example compounds according to formula (I) may be prepared by cyclisation of a compound of formula (V)

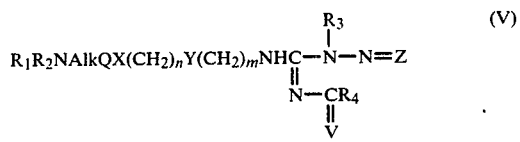

where V represents sulphur or more preferably oxygen and X represents two hydrogen atoms, in the absence of presence of a solvent, e.g. acetone or water, and optionally with heating.

It may be convenient to prepare in situ compounds of formula (V) in which Z represents two hydrogen atoms by treating a compound of formula (V) where Z represents a divalent protecting group which can readily be removed to yield two hydrogen atoms, for example a benzylidene group, with an acid, e.g. hydrochloric acid, preferably with heating and under such conditions cyclisation to give compounds of formula (I) will normally occur.

In a further embodiment of the cyclisation of compounds of formula (IV) compounds of formula (I) may also be prepared by cyclisation of a compound of formula (VI)

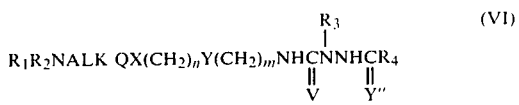

where V is NH and Y'' is sulphur, oxygen or NH, or V is sulphur or oxygen and Y'' is NH. The reaction is preferably carried out by heating the compound (VI) in a suitable solvent such as acetonitrile or dimethylformamide.

In a convenient embodiment of this process an intermediate of formula (VI) in which V is NH and Y'' is oxygen may be prepared in situ by the reaction of an aminoguanidine (VII)

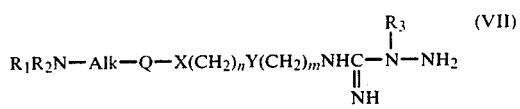

with an acid $R_4$COOH or with an activated derivative thereof as defined above.

The acid and the aminoguanidine (VII) may be heated together, under which conditions cyclisation of the intermediate (VI) takes place directly to give a compound of formula (I). In the case of an activated derivative an aprotic solvent, e.g. tetrahydrofuran may be used at temperatures from ambient to reflux. When using an acyl chloride as the activated derivative the reaction may also be carried out in the presence of a base e.g. a tertiary amine such as pyridine, which may also be used as the solvent.

In general intermediates of formulae (V) and (VI) may be prepared from diamines of the formula (III)

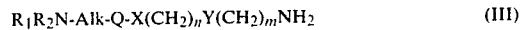

by methods analogous to those described in British Patent Specification Nos. 2047238A and 2023133A respectively.

The aminoguinidines (VII) may be prepared as described in British Patent Specification No. 2023133A.

Compounds of formula (I) may be prepared by reducing a compound of formula (VIII)

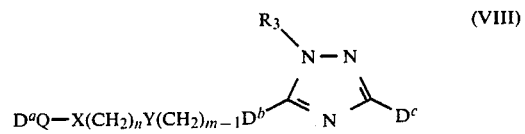

in which at least one of $D^a$, $D^b$ and $D^c$ represents a reducible group and the other(s) take the appropriate meaning corresponding to formula (I), where $D^a$ may represent $R_1R_2NAlk$ or a group convertible thereto under reducing conditions;

$D^b$ represents —CH$_2$NH—, —CONH— or —CH=N; and $D^c$ represents $R_4$ or a group convertible thereto under reducing conditions.

Thus for example compounds of formula (I) in which $R_6$ is hydroxymethyl or 1H-tetrazol-5-yl, and $R_7$ is 1H-tetrazol-5-yl, trifluoromethyl, heteroaryl, arylaminomethyl, aralkylaminomethyl, alkylthioalkyl, arylthioalkyl or the group $SO_2R_8$ or $CH_2NR_{18}SO_2R_{14}$ may be prepared by reducing an amide of formula (VIII) in which either $D^a$ represents $R_1R_2NAlk$ and $D^b$ represents —CONH—, or $D^a$ represents $R_1R_2NCO$ and $D^b$ represents —CH$_2$NH—, and $D^c$ represents $R_4$ or a group convertible thereto under the conditions of the reaction. Reduction may be effected using for example lithium aluminium hydride or aluminium hydride in a solvent such as tetrahydrofuran, dioxan or diethy ether.

In another embodiment of the reduction process an imine of formula (VIII) in which $D^a$ represents $R_1R_2NAlk$, $D^b$ represents —CH=N— and $D^c$ represents $R_4$ or a group convertible thereto under the conditions of the reaction may be reduced using for example a metal hydride such as an alkali or alkaline earth metal borohydride e.g. sodium borohydride in a solvent such as an alkanol e.g. methanol or ethanol, or aluminium hydride or lithium aluminium hydride in a solvent such as tetrahydrofuran or dioxan. Reduction of the imine (VIII) may also be effected using hydrogen and a suitable metal catalyst such as platinum, palladium or Raney nickel, in a solvent such as an alkanol e.g. methanol or ethanol.

In a further embodiment of the reduction process a compound of formula (I) ir which $R_4$ is the group $(CH_2)_pCH=CHR_6$ where $R_6$ represents hydroxymethyl may be prepared by reduction of an ester of formula (VIII) in which $D^a$ represents $R_1R_2NAlk$, $D^b$ represents —CH$_2$NH— and $D^c$ represents $(CH_2)_pCH=CHCOR_{19}$ where $R_{19}$ represents alkoxy. Reduction may be effected using for example lithium aluminium hydride or sodium bis(2-methoxyethyl)aluminium hydride.

In yet another embodiment of the reduction process a compound of formula (I) in which Alk is methylene may be prepared by treating an aldehyde of formula (VIII) in which $D^a$ represents CHO, $D^b$ represents —CH$_2$NH— and $D^c$ represents $R_4$ with ammonia or an amine $R_1R_2NH$ in a solvent such as tetrahydrofuran or an alkanol e.g. methanol or ethanol, followed by reduction using for example a hydride reducing agent such as an alkali or alkaline earth metal borohydride e.g. sodium borohydride, or aluminium hydride or lithium aluminium hydride, or with hydrogen and a metal catalyst such as palladium or platinum.

In the above embodiments it will be appreciated that in a process involving reductive alkylation of a compound of formula (VIII) in which $D^a$ represents CHO, or reduction of an imine (VIII) in which $D^b$ represents —CH=N—, the choice of reducing agent depends upon the nature of the group $R_4$, and the process may not be used for preparing compounds in which $R_6$ is $COR_{19}$ where $R_{19}$ represents hydrogen or alkyl, or where $R_7$ is —CH$_2$N=CHAryl or $COR_{11}$ where $R_{11}$ represents hydrogen, alkyl, aryl or aralkyl.

Amides and imines of formula (VIII) where $D^b$ is —CONH— or —CH=N—, $D^a$ is $R_1R_2NAlk$ or $R_1R_2NCO$ and $D^c$ is $R_4$ or a group convertible thereto may be prepared by methods analogous to those described in British Patent Specification No. 2047238A.

The compounds of formula (VIII) in which $D^a$ represents CHO, $D^b$ represents —CH$_2$NH and $D^c$ represents $R_4$ or a group convertible thereto may be prepared from an amine of formula (IX)

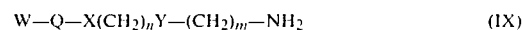

in which W represents a protected aldehyde group e.g. a cyclic acetal such as an ethylene acetal, by methods analogous to those described herein for preparing the corresponding compounds of formula (I).

Compounds of formula (I) in which q is zero and $R_7$ is an activating group such as nitro may be prepared by heating a diamine of formula (III) with a triazole of formula (X)

in which P is leaving group such as halogen e.g. bromine, and $R_7$ is as defined above, in the absence or presence of a solvent such as acetonitrile.

Compounds of formula (I) may also be prepared by introducing the group $R_1R_2NCH_2$— into the group Q present in a suitable intermediate. Thus compounds of formula (I) in which Alk represents a methylene group, Q represents a furan or substituted furan ring as defined in formula (I), and $R_4$ does not contain the group $CH_2NHC(=CHNO_2)NHR_{17}$, $CH_2N=CHAryl$, $COR_{11}$ (where $R_{11}$ is hydrogen, alkyl, aryl or aralkyl), or $COR_{19}$ (where $R_{19}$ is hydrogen or alkyl) may be prepared from a corresponding compound of formula (XI)

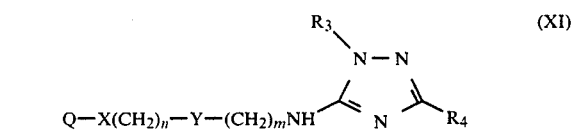

by a Mannich reaction using for example formaldehyde and an amine $R_1R_2NH$ or a salt thereof. The reaction may be carried out by reacting the amine salt with aqueous formaldehyde and the compound (XI) or by refluxing the amine salt with paraformaldehyde and the compound (XI) in a suitable solvent such as ethanol.

Compounds of formula (I) in which $R_4$ is the group $(CH_2)_qR_7$ in which $R_7$ is $COR_{11}$ where $R_{11}$ is hydrogen, hydroxy, alkyl, aryl or aralkyl, or $SO_2R_8$ may be prepared by oxidation of the corresponding compound in which $R_4$ is the group $(CH_2)_qCHR_{11}OH$, $(CH_2)_qCHO$, $(CH_2)_qSR_8$ (where $R_8$ is other than hydroxy) or $(CH_2)_qSH$.

Thus aldehydes and ketones of formula (I) in which $R_4$ is the group $(CH_2)_qCOR_{11}$ where $R_{11}$ is hydrogen, alkyl, aryl or aralkyl may be prepared by oxidising the corresponding hydroxyalkyl compound in which $R_4$ is $(CH_2)_qCHR_{11}OH$ using for example oxalyl chloride and dimethylsulphoxide, or activated manganese dioxide in a solvent such as dichloromethane.

Carboxylic acids of formula (I) in which $R_4$ is the group $(CH_2)_qCO_2H$ may be prepared by oxidising the corresponding aldehyde with e.g. silver oxide, in a solvent such as methanol.

Compounds of formula (I) in which $R_4$ is the group $(CH_2)_qSO_2R_8$ may be prepared by oxidising the corresponding compound in which $R_4$ is either $—(CH_2)_qSR_8$ (where $R_8$ is other than hydroxy) or $(CH_2)_qSH$ with for example peracetic acid or nitic acid. The reaction may be carried out in a solvent such as acetic acid, at room temperature.

The starting material in which $R_4$ is $(CH_2)_qSH$ where q is other than zero may be obtained by alkaline hydrolysis of the corresponding isothiourea, which may in turn be prepared by alkylating thiourea with an appropriate compound of formula (I) in which $R_7$ is a leaving group e.g. halo.

The thiol starting material in which $R_4$ is SH may be prepared by diazotisation of the corresponding aminotriazole followed by treatment with an alkali metal (e.g. potassium) salt of ethyl xanthate to give a xanthate in which $R_4$ is the group $—SC(=S)OEt$, which is subsequently hydrolysed (for example by heating with ethanolic potassium hydroxide) to give the starting thiol in which $R_4$ is the group SH.

The above oxidation process is particularly applicable to the preparation of compounds of formula (I) in which Q is a benzene or furan ring, X and Y are each oxygen, methylene or a bond, and there is no unsaturation within the groups $R_1$, $R_2$, $R_3$ and $R_4$.

Compounds of formula (I) in which $R_6$ is $CR^a{}_{19}=NR_{20}$ or $R_7$ is $CR^a{}_{11}=NR_{20}$ may be prepared by reacting the corresponding carbonyl compound with an appropriate reagent $H_2NR_{20}$ in a suitable solvent such as ethanol, optionally with heating.

Compounds of formula (I) in which $R_4$ is the group $CH=CHCOR_{19}$ where $R_{19}$ is alkyl or alkoxy may be prepared by treating the corresponding aldehyde in which $R_4$ is CHO with an appropriate compound containing an activated methylene group, for example by heating with a compound of formula $R_{19}COCH_2CO_2R_{22}$ (in which $R_{19}$ is alkyl or alkoxy and $R_{22}$ is alkyl e.g. ethyl) in a solvent such as pyridine or piperidine to give an intermediate of formula (I) in which $R_4$ is the group $CH=C(COR_{19})CO_2R_{20}$. Subsequent hydrolysis and decarboxylation for example by heating with methanolic potassium hydroxide, affords a product of formula (I) in which $R_4$ is $CH=CHCOR_{19}$ where $R_{19}$ is alkyl or alkoxy.

In a modification of the above process a compound of formula (I) in which $R_4$ is the group $CH=CHCOR_{19}$ where $R_{19}$ is hydroxy may be prepared by heating an aldehyde of formula (I) in which $R_4$ is CHO with malonic acid in a solvent such as pyridine or piperidine.

Compounds of formula (I) in which $R_4$ is the group $(CH_2)_pCH=CHCOR_{19}$ where $R_{19}$ is amino, alkylamino or dialkylamino, or $R_4$ is the group $(CH_2)_qR_7$ where $R_7$ is $SO_2NR_9R_{10}$ or $CONH_{12}R_{13}$ may be prepared by reacting an activated derivative of the corresponding carboxylic or sulphonic acid with ammonia or an appropriate amine $HNR_9R_{10}$ or $NHR_{12}R_{13}$. Suitable activated derivatives include those referred to previously e.g. acid chlorides or esters.

Amides and carboxylic acids of formula (I) in which $R_7$ is respectively $—CONH_2$ or $—CO_2H$ may be prepared by hydrolysis of the corresponding nitrile or ester.

Compounds of formula (I) in which $R_7$ is cyano and q is other than zero may be prepared by treating the corresponding compound in which $R_7$ is a leaving group such as a methanesulphonyloxy group with for example an alkali metal cyanide under aqueous conditions. The required methanesulphonate starting material may be prepared by treating the corresponding hydroxyalkyl derivative with an appropriate acid chloride such as methanesulphonyl chloride.

Compounds of formula (I) in which $R_7$ is cyano may be prepared by heating an oxime of formula (I) in which $R_7$ is the group $—CH=NOH$ with a dehydrating agent such as acetic anhydride.

Compounds of formula (I) in which $R_6$ or $R_7$ is a 1H-tetrazol-5-yl group may be prepared by treating the corresponding compound of formula (I) in which $R_6$ or $R_7$ is a cyano group with an alcohol (e.g. ethanol) in a concentrated mineral acid (e.g. hydrochloric acid) to give an intermediate imidate which may then be treated with sodium azide in a suitable solvent such as dimethylformamide.

Compounds of formula (I) in which $R_7$ is a monohalomethyl group may be prepared by treating the corresponding hydroxyalkyl compound with an appropriate acid halide, for example thionyl chloride.

Amines of formula (III) may be made by methods described in German Offenlegungsschrifts No. 2,734,070, 2,821,409 and 2,821,410 and British Patent Specification No. 2006771A or by methods analogous to those described therein. For example, amines of formula (III) in which X is oxygen or sulphur and Q is preferably a benzene ring may be prepared by reacting a compound of formula (XII)

$$R_1R_2NAlkQ—XH \qquad (XII)$$

with the phthalimide derivative (XIII)

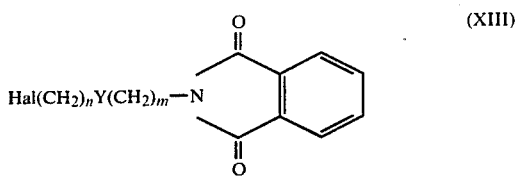

(XIII)

where Hal is chlorine or bromine, in the presence of a base followed by removal of the phthalimide protecting group.

Amines of formula (III) in which X is $—CH_2—$ may be prepared by reacting a compound of formula (XIV) with a compound of formula (XV)

$$R_1R_2NAlkQCH_2(CH_2)_nJ \qquad (XIV)$$

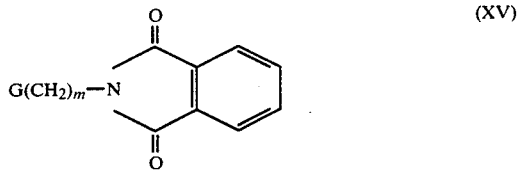

(XV)

where either J is a leaving group e.g. halogen and G is a hydroxyl or thiol group, or J is a hydroxyl or thiol group and G is a leaving group e.g. halogen. The reaction is carried out in the presence of a base e.g. sodium hydride or potassium carbonate, in a solvent such as dimethylformamide or acetone respectively, to give an intermediate of formula (XVI)

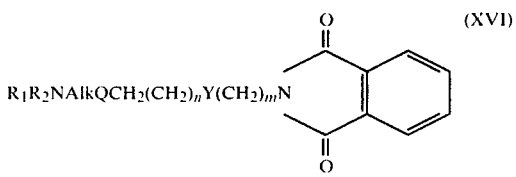

from which the amine (III) in which Z is —CH₂— may be formed by cleavage of the phthalimide protecting group.

Amines of formula (III) in which Q is a thiophen ring incorporated into the rest of the molecule through bonds at the 2- and 5-positions with an additional substituent $R_5$ adjacent to the group $R_1R_2NAlk$, or Q is a thiophen ring incorporated into the rest of the molecule through bonds at the 2- and 4-positions with an optional substituent $R_5$ adjacent to the group $R_1R_2NAlk$ (with the proviso that when the group $R_1R_2NAlk$ is in the 4-position then $R_5$ is in the 5-position), may be made by a number of methods depending on the precise structure of the compound.

Thus for example amines of formula (XVII)

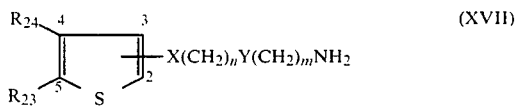

in which one of $R_{23}$ and $R_{24}$ represents the group $R_5$ and the other represents the group $R_1R_2NAlk$, X is a bond, n is 1 or 2, and Y is oxygen or sulphur may be prepared from the corresponding alcohol of formula (XVIII)

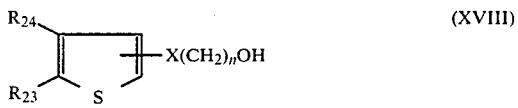

in which X is a bond and n is 1 or 2.

Thus amines of formula (XVII) in which X is a bond, n is 1 and Y is sulphur may be prepared by reacting an alcohol of formula (XVIII) in which X is a bond and n is 1 with an appropriate aminoalkane thiol salt (e.g. cysteamine hydrochloride) in a concentrated mineral acid (e.g. hydrochloric acid).

Amines of formula (XVII) in which X is a bond, n is 2 and Y is sulphur may be prepared by converting an alcohol of formula (XVIII) in which X is a bond and n is 2 into the corresponding haloalkyl compound using for example thionyl chloride or phosphorus tribromide, or mesylate by reaction with methanesulphonylchloride, followed by treatment with an appropriate aminoalkylthiol (e.g. cysteamine) in a solvent such as ethanol and in the presence of a base (e.g. sodium ethoxide).

Amines of formula (XVII) in which X is a bond, n is 1 or 2 and Y is oxygen may be prepared by treating an alcohol of formula (XVIII) in which X is a bond and n is 1 or 2 with a suitable base (e.g. potassium t-butoxide) in a solvent (e.g. dimethylformamide) followed by the addition of an appropriate haloalkylamine (e.g. chloropropylamine).

The alcohols of formula (XVIII), as well as the intermediates (XXX) and (XXXI) below, may be made by a variety of processes based on conventional methods in thiophene chemistry (Advances in Heterocyclic Chemistry Volume 1, 1963, page 2-116, Ed. A. R. Katritzky, Academic Press, London and New York; and Comprehensive Chemistry Volume 4, page 787, Ed. P G. Sammes, Pergamon Press, Oxford). Some representative routes and reagents are given in each case.

Alcohols of formula (XVIII) in which $R_{23}$ is the group $R_1R_2NCH_2$, X is a bond, n is 1 and the hydroxymethyl substituent is in either the 2- or 3-position may be prepared by treating a compound of formula (XIX)

with an amine $R_1R_2NH$ under reducing conditions as described previously for the preparation of compounds of the invention, to give a thiophenemethanamine of formula (XX) which may be subsequently reacted with paraformaldehyde in a concentrated mineral acid (e.g. hydrochloric acid) and acetic acid to introduce the hydroxymethyl group at either the 2- or 3-position.

Alcohols of formula (XVIII) in which $R_{24}$ is the group $R_1R_2NCH_2$, X is a bond, n is 1 and the hydroxymethyl substituent is at the 2-position may be prepared by reacting a compound of formula (XXI)

with for example oxalyl chloride in a solvent (e.g. benzene) and preferably in the presence of a catalyst (e.g. pyridine) followed by treatment with an amine $R_1R_2NH$ to give an amide of formula (XXII) which is subsequently reduced with a complex metal hydride e.g. lithium aluminium hydride in a solvent such as tetrahydrofuran to give a compound of formula (XXIII).

The 2-hydroxymethyl group is then introduced by reacting the compound of formula (XXIII) with formaldehyde or a precursor of formaldehyde such as paraformaldehyde, in a concentrated mineral acid, e.g. hydrochloric acid or acetic acid.

Alcohols of formula (XVIII) in which $R_{23}$ is the group $R_1R_2NCH_2$, $R_{24}$ is hydrogen, X is a bond, n is 1 and the hydroxymethyl substituent is in the 3-position may be prepared from a thiophene 3-carboxylate of formula (XXIV)

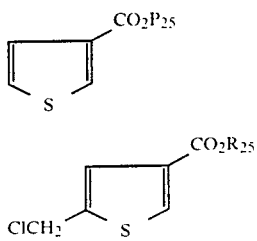

(XXIV)

(XXV)

where $R_{25}$ is an alkyl group. This compound is halomethylated e.g. chloromethylated using for example formaldehyde, or a precursor of formaldehyde such as paraformaldehyde, and gaseous hydrogen chloride in a solvent such as chloroform and in the presence of zinc chloride to give a compound of formula (XXV). The amino group $R_1R_2N$ is then introduced into the compound of formula (XXV) by reaction with an amine $R_1R_2NH$, in a suitable solvent such as ether, to give a compound of formula (XXVI)

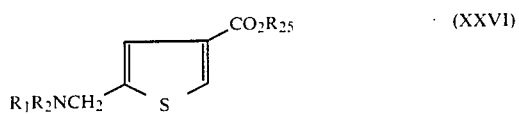

(XXVI)

which is then reduced using for example lithium aluminium hydride in a suitable solvent such as ether.

Alcohols of formula (XVIII) in which X is a bond and n is 2 may be prepared by lithiating a halothiophene of formula (XXVII)

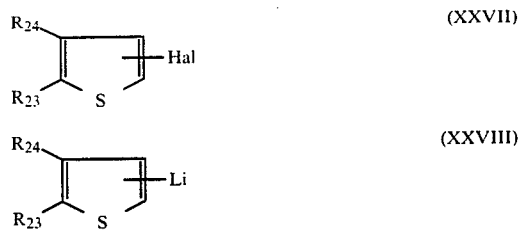

(XXVII)

(XXVIII)

(where Hal is halogen e.g. bromine) using n-butyl lithium in a suitable solvent (e.g. tetrahydrofuran) at a low temperature (e.g. $-78°$), followed by treatment of the resulting lithio derivative (XXVIII) with ethylene oxide in a solvent such as tetrahydrofuran, to give the desired hydroxyethyl compound (XVIII, X=bond and n=2).

In a modification of this process a halothiophene of formula (XXVII) in which $R_{23}$ is a group convertible to $R_1R_2NCH_2-$ (e.g. an aldehyde grouping protected as an acetal) and the group Hal is at the 3-position may be lithiated and treated with ethylene oxide as described above to give a hydroxyethyl compound of formula (XXIX).

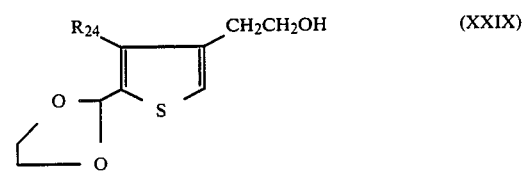

(XXIX)

Subsequent treatment with an amine $R_1R_2NH$ under reducing conditions as described previously for preparing compounds of the invention affords an alcohol of formula (XVIII) in which $R_{23}$ is the group $R_1R_2NCH_2$, X is a bond, n is 2 and the hydroxyethyl substituent is at the 3-position.

Amines of formula (XVII) in which X is a bond and Y is $CH_2$ may be prepared from an appropriate haloalkylthiophene of formula (XXX)

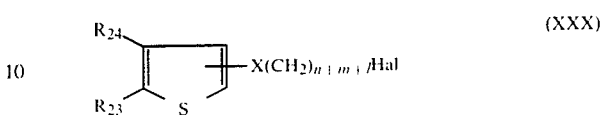

(XXX)

(in which X is a bond and Hal is halogen) by treatment with for example potassium phthalimide in a solvent (e.g. dimethylformamide), followed by deprotection of the phthalimido derivative using for example hydrazine hydrate.

The haloalkylthiophenes of formula (XXX) wherein X is a bond may be prepared for example by treating a lithio derivative of formula (XXVIII) with an α, ω-dihaloalkane (e.g. $Br(CH_2)_{n+m+1}Br$) in a solvent such as tetrahydrofuran to give an intermediate of formula (XXX).

Amines of formula (XVII) in which X is oxygen and n is 2 or 3 may be prepared from an appropriate alkoxythiphene (XXXI)

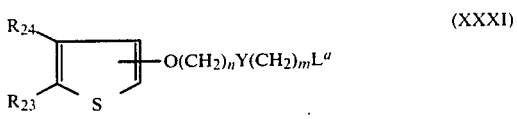

(XXXI)

where $L^a$ is a halogen atom (e.g. chlorine or bromine) or a leaving group (e.g. mesylate), by similar method to that described above for the preparation of amines of formula (XVII) in which X is a bond and Y is $CH_2$ from the corresponding haloalkyl thiophene.

Alkoxythiophenes of formula (XXXI) may be prepared for example by treating a halo (e.g. bromo) thiophene of formula (XXVII) with a diol $HO(CH_2)_nY(CH_2)_mOH$ where n is 2 or 3 in the presence of a base (e.g. sodium hydride) and cuprous oxide, and preferably with the addition of potassium iodide, to give a hydroxyalkoxy compound of formula (XXXII)

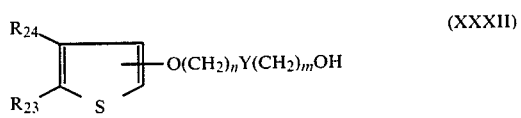

(XXXII)

(wherein n is 2 or 3) which may be treated with for example, thionyl chloride, phosphorus tribromide or methanesulphonyl chloride to give the alkoxythiophene of formula (XXXI).

Amines of formula (XVII) in which X is sulphur, and n is 2 or 3 may be prepared by treating a lithio derivative of formula (XXVII) with elemental sulphur, followed by reaction with an appropriate haloalkylamine $Hal(CH_2)_nY(CH_2)_mNH_2$ wherein n is 2 or 3 preferably in protected form, e.g. as a phthalimide with subsequent cleavage of the phthalimide group using for example hydrazine hydrate.

Where the product of any of the above processes is a free base and a salt is required, the salt may be formed in a conventional manner. Thus, for example, a generally convenient method of forming the salts is to mix appropriate quantities of the free base and the acid in an appropriate solvent(s) e.g. an alcohol such as ethanol or an ester such as ethyl acetate.

The invention is illustrated but not limited by the following Examples and Preparations.

In the following Examples and Preparations temperatures are in °C. "T.l.c." refers to thin layer chromatography and this and preparative chromatography where carried out on silica using, unless otherwise stated, one of the following solvent systems:
System A ethyl acetate:water:isopropanol:0.88 ammonia (25:4:15:1)
System B ethyl acetate:ethanol:0.88 ammonia (20:3:2)
System C Dichloromethane:ethanol:0.88 ammonia (50:8:1)
System D Methanol:0.88 ammonia (79.1)
System E ethyl acetate:water:isopropanol:0.88 ammonia (25:8:15:2).

PREPARATION 1

Methyl N[(1,3-dihydro-1,3-dioxo-2H-isoindol-2-yl)acetyl]-1-methyl-2-(phenylmethylene)hydrazinecarboximidothioate Methyl 1-methyl-2-(phenylmethylene)hydrazinecarboximidothioate hydroiodide (13.4 g) was suspended in a saturated aqueous solution of sodium carbonate and extracted with ethyl acetate. The organic extract was evaporated to leave a yellow oil (5.7 g) which was dissolved in acetone (180 ml) and treated with potassium carbonate (3.86 g) and 1,3-dioxo-2-isoindoline acetyl chloride (7.4 g). The suspension was stirred at room temperature for 18 h, heated at reflux for 3 h, and evaporated under reduced pressure. The residue was dissolved in water, saturated with sodium chloride, and the solution was washed with cyclohexane and ether, extracted with ethyl acetate and dichloromethane, and the organic extracts were evaporated to leave a pale yellow solid which was recrystallised from ethyl acetate to give the title compound (3.4 g) m.p. 182°.

PREPARATION 2

(a) Methyl N-[2-(methylthio)acetyl]-1-methyl-2-(phenylmethylene)hydrazine carboximidothioate (Methylthio)acetyl chloride (5.6 g) was added portionwise to a solution of methyl 1-methyl-2-(phenylmethylene)hydrazine carboximidothioate hydroiodide (A) (10.4 g) in triethylamine (7.08 g) and dichloromethane (55 ml) and the mixture stirred at room temperature for 2 h. The mixture was washed with water and evaporated to give an oil which was chromatographed using 1:1 ether-petroleum ether (b.p. 60°–80°) followed by ether to give the title compound (4.6 g) as a cream solid, m.p. 68°–70°.

(b) Similarly prepared from pyridine-2-carbonyl chloride hydrochloride (6 g) and methyl 1-methyl-2-(phenylmethylene)hydrazinecarboximidothioate hydrochloride (B) (10 g) in triethylamine (13 ml) and dichloromethane (50 ml), except that the crude product was crystallized from methyl acetate and petroleum ether (b.p. 60°–80°) was methyl 1-methyl-2-(phenylmethylene)-N-[2-(pyridinyl)carbonyl]hydrazinecarboximidothioate (1.6 g) as an off-white solid, m.p. 103° C.

(c) Similarly prepared from (phenylsulphonyl)acetyl chloride (4.4 g) and A (5.2 g) in triethylamine (6 ml) and dichloromethane (25 ml), except that the crude product was chromatographed using dichloromethane:methanol (50:1) and then triturated with methyl acetate, was methyl 1-methyl-2-(phenylmethylene)-N-[2-(phenylsulphonyl)acetyl]hydrazine carboximidothioate (1.1 g), m.p. 129.5°–130.5°.

(d) Similarly prepared from ethyl succinyl chloride (10.2 g) and A (17.25 g) in triethylamine (17 ml) and dichloromethane (50 ml), except that the crude product was triturated with ether and petroleum ether b.p. 60°–80° and recrystallised from ether, was ethyl-4-[[[1-methyl-2-(phenylmethylene)hydrazino](methylthio)-methylene]amino]-4-oxobutanoate (9.6 g) m.p. 51°–53°.

(e) Similarly prepared from 2-(acetoxy)propionyl chloride (5.25 g) and B (8 g) in triethylamine (10 ml) and dichloromethane (40 ml), except that the crude product was chromatographed using ethyl acetate:petroleum ether (b.p. 60°–80°) (1:1) and then crystallized from methyl acetate and petroluem ether (b.p. 60°–80°) was methyl N-[2-(acetyloxy-1-oxo-propyl]-1-methyl-2-(phenylmethylene)hydrazinecarboximidothioate (2.5 g) as a white solid, m.p. 89°.

(f) Similarly prepared from B (48.8 g) and 4-(1,3-dihydro-1,3-dioxo-2H-isoindol-2-yl)butyryl chloride (53.4 g) was methyl N-[4-[(1,3-dihydro-1,3-dioxo-2H-isoindol-2-yl)butyryl]]-1-methyl-2-(phenylmethylene)hydrazine carboximidothioate (44.7 g) as colourless plates from ethanol, m.p. 128°–129.5° C.

PREPARATION 3

(a) N-Amino-N'-[3-[3-(1-piperidinylmethyl)phenoxy]-propyl]guanidine hydrogen carbonate hemi-hydrate 3-[3-(1-Piperidinylmethyl)phenoxy]propanamine (A) (9.92 g) and methyl hydrazine carboximidothioate hydroiodide (B) (10.25 g) were heated together as a melt for 7 H at 80° then dissolved in toluene (50 ml) and heated for a further 2 h at 80°. The solution was cooled and washed with water. The aqueous layer was basified with 2N sodium bicarbonate resulting in a precipitate which was filtered off to give the title compound (4.2 g) as a buff coloured solid m.p. 115°.

(b) Similarly prepared from A (9.9 g) and B (9.3 g), but with the ommision of the basification step and formation of the hemi-tartrate salt in a ethyl acetate-ethanol solution, was N-Amino-N'-[3-[3-(1-piperidinylmethyl)phenoxy]propyl]quanidine hydroiodide hemi-tartrate (13.9 g), m.p. 55°.

PREPARATION 4

1-Methyl-3-trifluoromethyl-1H-1,2,4-triazole-5-amine

1-Amino-1-methyl guanidine sulphate (12.3 g) and trifluoroacetic acid (16 ml) were heated at reflux for 96 h. Excess trifluoroacetic acid was removed by distillation and the residue was basified with sodium bicarbonate and extracted with ethyl acetate. The extract was dried and evaporated to give a white solid (7.2 g) which was recrystallised from a mixture of methyl acetate (8 ml) and petroleum ether (b.p. 60°–80°) (20 ml) to give the title compound as a white powder (5.1 g) m.p. 165°–166°.

PREPARATION 5

(a)

1-Methyl-5[[3-[3-(1-piperidinylmethyl)phenoxy]propyl]amino]1H-1,2,4-triazole-3-methanamine N-[[1-Methyl-2-(phenylmethylene)hydrazino][[3-[3-(1-piperidinylmethyl)phenoxy]propyl]amino]methylene](1,3-dihydro-1,3-dioxo-2H-isoindol-2-yl)acetamide A solution of 3-[3-(1-piperidinylmethyl)phenoxy]propanamine (A) (1.96 g) and methyl N-[(1,3-dihydro-1,3-dioxo-2H-isoindol-2-yl)acetayl]-1-methyl-2-(phenylmethylene)hydrazinecarboximidothioate (B) (3.1 g) in acetonitrile (20 ml) was stirred at room temperature for 18 h. The solvent was evaporated to leave a yellow oil (5 g) which was crystallised from ether (600 ml), to give the title compound as a white solid (3.5 g), m.p. 84.5°.

1-Methyl-5[[3-[3-(1-piperidinylmethyl)phenoxy]propyl]amino]1H-1,2,4-triazole-3-methanamine A solution of the above acetamide (3.4 g) acetone (100 ml) and 2N hydrochloric acid (15 ml) was heated at reflux for 17 h. The solution was diluted with water (20 ml) and evaporated under reduced pressure to a volume of 50 ml. The aqueous solution was washed with ethyl acetate, basified with sodium carbonate, and extracted with ethyl acetate. The organic extracts were evaporated to leave a yellow oil (2.7 g) which was used without further purification. The oil (1.2 g) was dissolved in ethanol (15 ml), and stirred at room temperature with hydrazine hydrate (0.5 g) for 24 h. The solvent was removed under reduced pressure, and the residue was dissolved in aqueous sodium carbonate. The aqueous solution was washed with ether treated with 2N sodium hydroxide and extracted with ethyl acetate. The organic extracts were evaporated to leave the title compound as a pale yellow oil (0.51 g). T.l.c. System B (20:3:2) R$_f$0.25.

(b) Similarly prepared from methyl N-[4-[(1,3-dihydro-1,3-dioxo-2H-isoindol-2-yl)butyryl]]-1-methyl-2-(phenylmethylene)hydrazine carboximidothioate (21.1 g) and A (15.3 g), but using ethanolic methylamine instead of hydrazine (as in Preparation 8), was 1-methyl-5-[[3-[3-(1-piperidinylmethyl)phenoxy]propyl]amino]-1H-1,2,4-triazole-3-propanamine as a gum (1.8 g). T.l.c. System C, Rf 0.06.

(c) Similarly prepared from B (1.5 g) and 5-[[2-(amino)ethyl]thio]methyl-N,N-3-trimethylthiophenemethanamine (1.0 g) was 2-[[5-[[2-[[[5-[(dimethylamino)methyl]-4-methyl-2-thienyl]methyl]thio]ethyl]amino]-1-methyl-1H-1,2,4-triazol-3-yl]methyl]-1H-isoindole-1,3(2H)-dione (1.2 g) with the exceptions that the cyclisation was effected by heating the reaction mixture in acetone at 80° for 1 h with 2N hydrochloric acid and the crude product was purified by column chromatography (System C). T.l.c. System C Rf 0.85.

The above 1H-isoindole-1,3(2H)-dione (1.1 g) gave 1-methyl-5-[[2-[[[5-[(dimethylamino)methyl]-4-methyl-2-thienyl]methyl]thio]ethyl]amino]-1H-1,2,4-triazole-3-methanamine (0.6 g) except that ethanolic methylamine was used instead of hydrazine (as in Preparation 8) and the crude product was purified by column chromatography (dichloromethane:ethanol:0.88 ammonia 40:8:1). T.l.c. System C Rf 0.35.

PREPARATION 6

(a)

2-[(1,3-Dihydro-1,3-dioxo-2H-isoindol-2-yl)amino]-N-[[[2-[[5-[(dimethylamino)methyl]-2-furanylmethyl]thio]ethyl]amino][1-methyl-2-(phenylmethylene)hydrazino]methylene]acetamide A solution of 2[[5-[(Dimethylamino)methyl]-2-furanylmethyl]thio]ethylamine (2.1 g) and methyl N-[(1,3,-dihydro-1,3-dioxo-2H-isoindol-2-yl)acetyl]-1-methyl-2-(phenylmethylene)hydrazinecarboximidothioate (B) (3.9 g) in acetonitrile (30 ml) was stirred at 25° C. for 18 h. The white solid which resulted was filtered off and washed with acetonitrile (2 × 10 ml) to give the title compound (3.0 g) as a white solid, m.p. 115°.

The following compounds were similarly prepared from Compound B and the appropriate amine.

(b) Compound B (2 g) and 3[3-[(dimethylamino)methyl]phenoxy]propanamine (1 g) gave 2-[(1,3,-dihydro-1,3,dioxo-2H-isoindo2-yl)amino]-N-[[[3-[3-[(dimethylamino)methyl]phenoxy]propyl]amino][1-methyl-2-(phenylmethylene)hydrazino]methylene]acetamide (2.5 g) as a pale yellow foam. T.l.c. System E. Rf 0.7.

(c) Compound B (2.0 g) and 2[2-[3-(1piperidinylmethyl)phenoxy]ethoxy]ethylamine (1.4 g) gave 2-[(1,3-dihydro-1,3,dioxo-2H-isoindol-2-yl)amino]-N-[[1-methyl-2-(phenylmethylene)hydrazino][2-[2-[3-(1-piperidinylmethyl)phenoxy]ethoxy]ethyl]amino]methylene]acetamide (3.1 g) as a pale yellow gum. T.l.c. System B Rf 0.65.

(d) Compound B (2.0 g) and 3-[(N,N-dimethylamino)methyl]benzenebutanamide (1.1 g) gave N-[[[4-[3-(dimethylaminomethyl)phenyl]butyl]amino]methylene][1-methyl-2-(phenylmethylene)hydrazino](1,3,-dihydro-1,3,dioxo-2H-isoindol-2-yl)acetamide (2.8 g) as a white solid mp 123°-126°.

PREPARATION 7

(a)

2-[[5-[[2-[[5-[(Dimethylamino)methyl]-2-furanylmethyl]thio]ethyl]amino]-1-methyl-1H-1,2,4-triazol-3-yl]methyl]-1H-isoindole-1,3(2H)-dione 2-[(1,3-Dihydro-1,3-dioxo-2H-isoindol-2-yl)amino]-N-[[[2-[[5-[(dimethylamino)methyl]-2-furanylmethyl]thio]ethyl]amino][1-methyl-2-(phenylmethylene)hydrazino]methylene]acetamide (2.82 g) was dissolved in 2N hydrochloric acid (9 ml) and toluene (5 ml) and stirred at 40°-50° for 18 h. The phases were separated and the inorganic phase washed with toluene, basified with sodium carbonate solution and extracted with ethyl acetate. The extract was evaporated to give the title compound (2.28 g) as a pale yellow oil. T.l.c. System A, Rf 0.55.

The following triazoles were similarly prepared from the corresponding acetamides.

(b) 2-[(1,3-Dihydro-1,3-dioxo-2H-isoindol-2-yl)amino]-N-[[[3-[3-[(dimethylamino)methyl]phenoxy]propyl]amino][1-methyl-2-(phenylmethylene)hydrazino]methylene]acetamide (2.5 g) gave 2-[[5-[[3-[3-[(dimethylamino)methyl]phenoxy]propyl]amino]-1-methyl-1H-1,2,4-triazol-3-yl]methyl]-1H-isoindole-1,3(2H)-dione (1.85 g) as an off white foam. T.l.c. System A, Rf 0.6.

(c) 2-[(1,3-Dihydro-1,3-dioxo-2H-isoindol-2-yl)amino]-N-[[1-methyl-2-(phenylmethylene)hydrazino][2-[2-[3-(1-piperidinylmethyl)phenoxy]ethoxy]ethyl]amino]methylene]acetamide (3.1 g) gave 2-[1- methyl-[5-[2-[[2-[3-(1-piperidinylmethyl)phenoxy]ethoxy]ethyl]amino]-1H-1,2,4-triazol-3-yl]methyl]-1H-isoindole-1,3-(2H)-dione (2.4 g) as a pale yellow solid. T.l.c. System B Rf 0.55.

(d) N-[[[4-[3-(dimethylaminomethyl)phenyl]butyl]amino]methylene][1-methyl-2-(phenylmethylene)hydrazino](1,3-dihydro-1,3-dioxo-2H-isoindol-2-yl)acetamide (2.8 g) gave 3-[(1,3-dihydro-1,3-dioxo-2H-isoindol-2-yl)methyl]-N-[4-[3-(dimethylaminomethyl)phenyl]butyl]-1-methyl-1H-1,2,4-triazol-5-amine as a brown gum (1.45 g) T.l.c. System D Rf 0.47.

PREPARATION 8

(a)
5-[[2-[[5-[(Dimethylamino)methyl]-2-furanylmethyl]thio]ethyl]amino]-1-methyl-1H-1,2,4-triazole-3-methanamine 2-[[5-[[2-[[5-[(Dimethylamino)methyl]-2-furanylmethyl]thio]ethyl]amine]-1-methyl-1H-1,2,4-triazol-3-yl]methyl]-1H-isoindole-1,3(2H)-dione (2.2 g) in ethanol (25 ml) was treated with ethanolic methylamine (33% w/v, 7 ml) and the mixture was stirred at room temperature for 3 h. The mixture was evaporated and the residue partitioned between 2N sodium hydroxide and ethyl acetate. The organic phase was washed with 5N sodium hydroxide and evaporated to give the title compound (1.5 g) as a pale brown oil. T.l.c. System A, Rf 0.3.

The following 3-aminomethyl triazoles were similarly prepared from the corresponding isoindole-1,3(2H)-diones.

(b) 2-[[5-[[3-[3-[(Dimethylamino)methyl]phenoxy]propyl]amino]-1-methyl-1H-1,2,4-triazol-3-yl]methyl]-1H-isoindole-1,3 (2H) dione (1.8 g) gave 5-[[3-[3-[(dimethylamino)methyl]phenoxy]propyl]amino]-1-methyl-1H-1,2,4-triazole-3-methanamine (1.1 g) as a pale yellow oil. T.l.c. System B, Rf 0.4.

(c) 2-[1-Methyl-[5-[2-[[2-[3-(1-piperidinylmethyl)-phenoxy]ethoxy]ethyl]amino]-1H-1,2,4-triazol-3-yl]methyl]-1H-isoindole-1,3 (2H)-dione (2.4 g) gave 1-methyl-5-[2-[[2-[3-(1-piperidinylmethyl)phenoxy]ethoxy]ethyl]amino]-1H-1,2,4-triazole-3-methanamine (1.37 g) as a pale yellow oil. T.l.c. System B Rf 0.25.

(d) 3-[(1,3-dihydro-1,3-dioxo-2H-isoindol-2-yl)methyl]-N-[4-[3-(dimethylaminomethyl)phenyl]butyl]-1-methyl-1H-1,2,4-triazol-5-amine (1.45 g) gave 5-[[4-[3-[(dimethylamino)methyl]phenyl]butyl]amino]-1-methyl-1H-1,2,4-triazole-3-methanamine (1.1 g) as a brown gum. T.l.c. System D Rf. 0.25.

PREPARATION 9

3-[3-[[1-Methyl-3-[(phenylsulphonyl)methyl]-1H-1,2,4-triazol-5-yl]amino]propoxy]benzaldehyde.

A mixture of 3-[3-(1,3-dioxolan-2-yl)phenoxy]propanamine (2.3 g) and methyl-1-methyl-2-(phenylmethylene)-N-[2-(phenylsulphonyl)acetyl]hydrazine carboximidothioate (4.0 g) was heated at 60° under water pump vacuum for 3 h. The reaction mixture was dissolved in toluene (100 ml), 5N hydrochloric acid (100 ml) and acetone (50 ml) and stirred at room temperature for 18 h. The aqueous layer was basified to pH 9 with potassium carbonate and extracted with ethyl acetate. The organic extract was evaporated to give the title compound as an amber gum (3.0 g) T.l.c. Methanol; Rf 0.8.

PREPARATION 10

4-[[2-(Amino)ethyl]thio]methyl-N,N-dimethyl-2-thiophenemethanamine

Methyl 5-(dimethylaminomethyl)-3-thiophene carboxylate

A solution of methyl 5-(chloromethyl)-3-thiophenecarboxylate (1.9 g) in dry diethylether (100 ml) was treated with anhydrous dimethylamine (5 ml). After 6 hours the solvent was removed in vacuo and the residue was dissolved in 5M hydrochloric acid (20 ml). The aqueous solution was washed with diethylether, basified with 5M sodium hydroxide (30 ml) and extracted with ether. The ethereal extracts were evaporated to give an oily residue which was distilled to yield the title compound as a colourless oil (1.6 g) b.p. 120°–130°/0.5 mm.

5-(Dimethylaminomethyl)-3-thiophenemethanol

A solution of the above thiophenecarboxylate (1.5 g) in diethylether (50 ml) was treated with lithium aluminium hydride (0.21 g). After 1 hour water (2 ml) was added and the solution was filtered through diatomaceous earth. Evaporation of the filtrate gave an oily residue which distilled to give the title compound as an oil (1.2 g) b.p. 120°/0.1 mm.

4-[[2-(Amino)ethyl]thio]methyl-N,N-dimethyl-2-thiophenemethanamine

A mixture of the above thiophenemethanol (1 g) and 2-aminoethanethiol hydrochloride (0.67 g) was stirred in concentrated hydrochloric acid (7 ml) at 0° C. for 2 hours; and then at room temperature for 48 hours. Solid anhydrous sodium carbonate was added and the product was extracted into ethyl acetate.

The organic extract was distilled to give the title compound as a colourless oil (0.75 g) b.p. 130°/0.05 mm.

PREPARATION 11

5-[[2-(Amino)ethyl]thio]methyl]-N,N-3-trimethylthiophenemethanamine 5-(Dimethylaminomethyl)-4-methyl-2-thiophenemethanol A solution of N,N-3-trimethyl-2-thiophenemethanamine (1.5 g) in dry tetrahydrofuran (50 ml) was treated with a solution of n-butyl lithium (1.6M; 7 ml) at room temperature, under nitrogen. After 4 h, gaseous formaldehyde (excess) was added and the mixture was heated at 40° C. for 20 h.

Water (100 ml) and chloroform (100 ml) were added and the organic solution evaporated in vacuo to leave an oily residue which was dissolved in ethanol (50 ml) and treated with sodium borohydride (0.1 g), followed by acetic acid (10 ml). The reaction mixture was evaporated to dryness and the residue was dissolved in sodium carbonate solution (8%; 50 ml) and extracted with chloroform. The organic extract was distilled to give the title compound as a colourless oil (0.65 g) b.p. 120°/0.1 mm.

Following the method of Preparation 10, 2-aminoethanethiol hydrochloride (0.6 g) and the above thiophenemethanol (0.6 g) gave 5-[[2-(amino)ethyl]thio]methyl-N,N,3-trimethylthiophenemethanamine as a colourless oil (0.69 g) b.p. 150°/0.1 mm.

PREPARATION 12

2-[2-[3-(1-piperidinylmethyl)phenoxy]ethoxy]ethylamine

A solution of 3-[1-piperidinylmethyl]phenol (2.7 g) and sodium hydride (0.34 g) in dry dimethylformamide (100 ml) was stirred at 25° during 6 h under nitrogen. 2-[2-(2-Chloroethoxy)ethyl]-1H-isoindole-1,3-(2H)-dione (3.6 g) was added and the mixture was stirred at 25° during 12 h and at 80° during 2 h. The cooled mixture was poured onto water and extracted with ether. The solvent was evaporated to leave a crude oil (5.1 g) which was used without further purification.

This oil and hydrazine hydrate (1.0 g) were heated under reflux in ethanol (100 ml) for 2 h and then cooled to 25°. Ether was added and the precipitate which formed was removed by filtration. The filtrate was concentrated in vacuo to give the title compound (2 g) b.p. 180° (0.1 mm).

PREPARATION 13

Methyl 1-methyl-N-[(methylsulphonyl)acetyl]-2-(phenylmethylene)hydrazinecarboximidothioate To a stirred solution of methyl 1-methyl-2-(phenylmethylene)hydrazinecarboximidothioate hydrochloride (5.71 g) and triethylamine (5.2 g) in dichloromethane (100 ml) was added methylsulphonylacetyl chloride (4.9 g) in dichloromethane (20 ml) dropwise during 0.5 h at 20°. The mixture was stirred at 20° during 18 h, water (100 ml) added and the phase separated. The dichloromethane layer was washed with water, dried, and evaporated. The residue was crystallised from ethanol to give the title compound (2.7 g) as off white needles. m.p. 149.5°–150.5°.

EXAMPLE 1

(a)

1-Methyl-3-methylthiomethyl-N-[3-[3-(1-piperidinylmethyl)phenoxy]propyl]-1H-1,2,4-triazole dihydro chloride hemihydrate Methyl N-[2-(methylthio)acetyl]-1-methyl-2-(phenylmethylene)hydrazine carboximidothioate (2.95 g) and 3-[3-(1-piperidinylmethyl)phenoxy]propanamine (2.48 g) were heated at 55° under water vacuum for 1 h. Additional carboximidothioate (0.3 g) was then added and the mixture heated for a further 0.5 h. The reaction mixture was dissolved in toluene (15 ml) and 5N hydrochloric acid (12 ml), and stirred at room temperature for 18 h and the phases separated. The aqueous phase was basified to pH 8 with sodium bicarbonate solution, washed with toluene, basified to pH 10 with sodium carbonate and extracted with ethyl acetate to give an oil, which was chromatographed using 3:1 ethyl acetate-methanol to give an oil (3.1 g). This oil (1.27 g) was dissolved in ether and treated with ethereal hydrogen chloride to give a white solid which was recrystallised from ethyl acetate-methanol to give the title compound (0.37 g) as white crystals m.p. 158°–160°.

Found: C, 50.9; H, 7.1; N, 14.6; $C_{20}H_{31}N_5OS.2HCl.1/2H_2O$ requires: C, 50.9; H, 7.3; N, 14.6%.

(b) Similarly prepared from 3-[3-(1-piperidinylmethyl)phenoxy]propanamine (0.58 g) and methyl 1-methyl-2-(phenylmethylene)-N-[2-(phenylsulphonyl)acetyl]-hydrazine carboximidothioate (A), (1.1 g) was 1-methyl-3-phenylsulphonylmethyl-N-[3-[3-(1-piperidinylmethyl)phenoxy]propyl]-1H-1,2,4-triazole-5-amine dihydrochloride hydrate (1.0 g), m.p. 120°–123°.

Found: C, 52.3; H, 6.2; N, 11.7; $C_{25}H_{33}N_5O_3S.2HCl.H_2O$ requires: C, 52.3; H, 6.5; N, 12.2%

(c) Similarly prepared from 3-[3-(1-piperidinylmethyl)phenoxy]propanamine (0.50 g) and methyl 1-methyl-2-(phenylmethylene)-N-[2-(pyridinyl)carbonyl]hydrazine carboximidothioate (0.69 g), except that column chromatography was not necessary, was 1-methyl-3-[3-(1-piperidinylmethyl)phenoxy]propyl]-3-(2-pyridinyl)-1H-1,2,4-triazole-5-amine (0.7 g). T.l.c system A, Rf 0.75.

Nmr (CDCl₃): 2.28, dd, (1H); 2.9, dd, (1H); 2.23 dt, (1H); 2.75; dt+t, (2H); 2.9–3.0, m, (3H); 5.35, brt, (1H); 5.82, t, (2H); 6.30–6.33, q+s, (5H); 6.57. s, (2H); 7.5–7.8, m, (6H); 8.5, m, (6H).

(d) Similarly prepared from 4-[[2-(aminoethyl)thio]-methyl]-N,N-dimethyl-2-thiophenemethanamine (0.54 g) and A (1 g) was 1-methyl-3-(phenylsulphonyl)methyl-N-[2-[[5-(dimethylamino)methyl-3-thienylmethyl]-thio]ethyl]-1H-1,2,4-triazole-5-amine (1.0 g) as a pale orange-brown oil.

Nmr (CDCl₃): 2.1, m, (2H); 2.3–2.6, m, (3H); 3.0, s, (1H); 3.15, s, (1H); 5.7, s, (2H); ca. 5.7, br t, (1H); 6.4, s, (2H); 6.47, s, (2H); 6.54, s, (3H); 6.64, q, (2H); 7.42, t, (2H); 7.78, s, (6H).

Ir (smear): 3380 cm⁻¹, 1318, 1158.

EXAMPLE 2

(a)

N-[[1-methyl-5-[[3-[3-(1-piperidinylmethyl)phenoxy]-propyl]amino]-1H-1,2,4-triazole-3-yl]methyl]acetamide.

A solution of acetic anhydride (0.089 g) in dry pyridine (1 ml) was added dropwise to a solution of 1-methyl-5-[[3-[3-(1-piperidinylmethyl)phenoxy]propyl]amino]-1H-1,2,4-triazole-3-methanamine (A) (0.31 g) at 5°. The solution was stirred at room temperature for 0.5 h, and the solvent was removed under reduced pressure to leave a yellow oil which was triturated with light petroleum b.p. 60°–80° to give the title compound as a white solid (0.27 g), m.p. 123°.

Analysis Found: C, 63.1; H, 8.1; N, 20.7; $C_{21}H_{32}N_6O_2$ requires: C, 63.0; H, 8.05; N, 21.0%.

The following compounds were similarly prepared:

(b) A (0.5 g) and trifluoroacetic anhydride (0.29 g) gave 2,2,2-trifluoro-N-[[1-methyl-5-[[3-[3-(1-piperidinylmethyl)phenoxy]propyl]amino]-1H-1,2,4-triazol-3-yl]methyl]acetamide (260 mg). T.l.c. System A Rf. 0.7.

Nmr (CDCl₃): 2.77–3.3, m+t, (5H); 5.49–5.62, d, (3H); 5.90, t, (2H); 6.45–6.60, q+s+s, (7H); 7.67–7.90, m+m, (6H); 8.6, m, (6H).

(c) 5-[[2-[[5-[(dimethylamino)methyl]-2-furanylmethyl]thio]ethyl]amino]-1-methyl-1H-1,2,4-triazole-3-methanamine (0.75 g) and acetic anhydride (0.23 ml) gave N-[[5-[[2-[[5-[(Dimethylamino)methyl]-2-furanylmethyl]thio]ethyl]amino]-1-ethyl-1H-1,2,4-triazol-3-yl]methyl]acetamide (0.6 g) as a brown gum. T.l.c. System D. Rf 0.48.

Nmr (CDCl₃): 3.8–3.9, brs, (3H); 5.3, brt, (1H); 6.3, s, (2H); 6.49–6.60, s+q, (7H); 7.2, t, (2H); 7.8, s, (6H); 8.0, s, (3H).

(d) 5-[[4-[3-[(dimethylamino)methyl]phenyl]butyl]amino]-1-methyl-1H-1,2,4-triazole-3-methanamine (1.1 g) and acetic anhydride (0.35 ml) gave N-[[5-[[4-[3-[(dimethylamino)methyl]phenyl]butyl]amino]-1-methyl-1H-1,2,4-triazol-3-yl]methyl]acetamide (1.0 g). T.l.c. System D, Rf 0.44.

Nmr (CDCl$_3$): 2.7–3.0, m, (4H); 3.60, br, (1H); 5.67, d, (2H); 5.77, t, (1H); 6.50–6.60, 2×s+q, (7H); 7.32, t, (2H); 7.74, s, (6H); 8.00, s, (3H); 8.30, m, (4H).

(e) 1-Methyl-5-[[2-[[[5-[(dimethylamino)methyl]-4-methyl-2-thienyl]methyl]thio]ethyl]amino]1H-1,2,4-triazole-3-methanamine (0.55 g) and acetic anhydride (1.6 g) gave N-[[1-methyl-5-[[2-[[[5-[(dimethylamino)methyl]-4-methyl-2-thienyl]methyl]thio]ethyl]amino]-1H-1,2,4-triazol-3-yl]methyl]acetamide (0.32 g). T.l.c. System C, Rf 0.42.

Nmr (CDCl$_3$): 3.35, s, (1H); 3.80, s, (1H); 5.50, t, (1H); 5.65 d, (2H); 6.12, s, (2H); 6.4–6.6, m, (7H); 7.20, t, (2H); 7.73, s, (6H); 7.90, s, (3H); 7.98, s, (3H).

EXAMPLE 3

1-Methyl-3-nitro-N-[3-[3-(1-piperidinylmethyl)phenoxy]propyl]-1H-1,2,4-triazole-5-amine

5-Bromo-1-methyl-3-nitro-1H-1,2,4-triazole

A stirred solution of 3-bromo-5-nitro-1H-1,2,4-triazole (13.1 g) in acetone (100 ml) was cooled to 0° and treated with 10% sodium hydroxide solution (30 ml), followed by dimethyl sulphate (9.5 g). After 18 h at room temperature, the mixture was evaporated in vacuo; the residue was diluted with water and extracted with ethyl acetate. The combined extracts were washed with 2N sodium hydroxide solution, water, and evaporated in vacuo. The resulting solid was recrystallized from a mixture of ethyl acetate and cyclohexane to yield the title compound (6.0 g), m.p. 90.5°–91.5°.

1-Methyl-3-nitro-N-[3-[3-(1-piperidinylmethyl)phenoxy]propyl]-1H-1,2,4-triazole-5-amine The above triazole (0.414 g) and 3-[3-(1-piperidinylmethyl)phenoxy]propanamine (1.0 g) were heated together under nitrogen at 80° for 1 h. The resulting oil was chromatographed using methanol as eluant to give the title compound as an oil (0.6 g). T.l.c. System E. R$_f$ 0.8.

Nmr (CDCl$_3$) 2.72, m, (1H); 3.0–3.3, m, (3H); 4.72, t, (1H); 5.83, t, (2H); 6.28, s+q (5H); 6.50, s, (2H); 7.4–7.7 and 7.83, m, (total 6H); 8.2–8.7, m, (6H).

EXAMPLE 4

(a)

1-methyl-5-[[4-[3-(1-piperidinylmethyl)phenoxy]butyl]amino]-1H-1,2,4-triazole-3-carboxaldehyde Dimethyl sulphoxide (304 mg) was added to a solution of oxalyl chloride (254 mg) in dichloromethane (20 ml) at −60° under nitrogen for 2 min. and a solution of 1-methyl-5-[[4-[3-(1-piperidinylmethyl)phenoxy]butyl]amino]-1H-1,2,4-triazole-3-methanol (0.5 g) in dichloromethane (10 ml) was added. The mixture was stirred at −50° to −60° for 15 min. and then quenched with triethylamine (657 mg). The solution was allowed to warm to 25° and was diluted with water. The aqueous phase was extracted with dichloromethane and the combined organic extracts were dried and evaporated to leave the title compound as a pale yellow oil (0.4 g).

Nmr (CDCl$_3$) 0.2, s, (1H); 2.78, t, (1H); 3.0–3.3, m, (3H); 5.25, br, t, (B 1H); 6.06, br, t, (2H); 6.40, s, (3H); 6.5, q, (2H); 6.60, s, (2H), 7.68, br, (4H); 8.0–8.6, m, (10H). T.l.c. System D R$_f$ 0.55.

(b) Similarly 1-methyl-5-[[3-[3-(1-piperidinylmethyl)phenoy]propyl]amino]-1H-1,2,4-triazole-3-methanol (4 g), oxalyl chloride (2.03 g) and dimethyl sulphoxide (2.43 g) gave 1-Methyl-5-[[3-[3-(1-piperidinylmethyl)phenoxy]propyl]amino]-1H-1,2,4-triazole-3-carboxaldehyde (2.54 g), m.p. 91°–2°.

Found: C, 63.5; H, 7.5; N, 19.3; C$_{19}$H$_{27}$N$_5$O$_2$ requires: C, 63.8; H, 7.6; N, 19.6%.

EXAMPLE 5

Ethyl 5-[4-[3-(1-piperidinylmethyl)phenoxy]butyl]amino-1H-1,2,4-triazole-3-carboxylate Methyl 5-amino-1H-1,2,4-triazole-3-carboxylate (0.568 g) and 4-[3-(1-piperidinylmethyl)phenoxy]butanal in ethanol (40 ml) were heated at reflux for 2 h. The cooled reaction mixture was treated with sodium borohydride (0.4 g) and stirred at room temperature for 15 h. The solvent was evaporated and the residue was dissolved in 2N hydrochloric acid which was washed with ethyl acetate, basified with sodium carbonate and extracted with ethyl acetate. The combined organic extracts were evaporated to yield the title compound as a white solid which was recrystallised from a mixture of ethyl acetate and ethanol (1:1) (0.5 g) m.p. 170°–1° dec.

Found: C, 62.6; H, 7.6; N, 17.2; C$_{21}$H$_{31}$N$_5$O$_3$ requires: C, 62.8; H, 7.8; N, 17.4%.

EXAMPLE 6

5-[4-[3-(1-Piperidinylmethyl)phenoxy]butyl]amino-1H-1,2,4-triazole-3-carboxamide A suspension of ethyl 5-[4-[3-(1-piperidinylmethyl)phenoxy]butyl]amino-1H-1,2,4-triazole-3-carboxylate (867 mg) in 0.88 ammonia (25 ml) was stirred at room temperature for 18 h. The mixture was evaporated and the residual solid was washed with boiling methanol to leave the title compound as a white solid (255 mg) m.p. 212°–4° dec.

Found: C, 61.3; H, 7.6; N, 22.3; C$_{19}$H$_{28}$N$_6$O$_2$ requires: C, 61.3; H, 7.6; N, 22.6%.

EXAMPLE 7

1-Methyl-5-[[3-[3-(1-piperidinylmethyl)phenoxy]propyl]amino]-1H-1,2,4-triazole-3-carboxylic acid hemitartrate sesquihydrate A solution of 1-methyl-5-[[3-[3-(1-piperidinylmethyl)phenoxy]propyl]amino]-1H-1,2,4-triazole-3-carboxaldehyde (1.07 g) in methanol was treated with silver oxide (3 g). The mixture was stirred for 19 h at room temperature, and then chromatographed using methanol. The crude acid was dissolved in water (charcoaled), filtered and evaporated. The solid residue was dissolved in hot methanol and isopropanol. The cooled solution was purified by filtration and the filtrate was evaporated. The residue was dissolved in ethanol and treated with a solution of tartaric acid in ethanol. The resulting solid was collected by filtration to give the title compound (0.43 g), m.p. 130° (softens).

Found: C, 53.4; H, 6.60; N, 14.8; C$_{19}$H$_{27}$N$_5$O$_3$.½C$_4$H$_6$O$_6$.1½H$_2$O requires: C, 53.1; H, 6.98; N, 14.7%.

EXAMPLE 8

(a)

1-Methyl-5-[[3-[3-(1-piperidinylmethyl)phenoxy]propyl]amino]-1H-1,2,4-triazole-3-carboxamide tartrate dihydrate A mixture of 1-methyl-5-[[3-[3-(1-piperidinylmethyl)phenoxy]propyl]amino]-1H-1,2,4-triazole-3-carboxylic acid (0.5 g), dimethylformamide (0.05 g), thionyl chloride (0.5 ml) and dry dichloromethane (10 ml) was stirred at room temperature for 2 hours. Ammonia gas was passed through the reaction mixture for 1 hour. Water was added and the product was extracted with dichloromethane. The extract was dried, filtered and evaporated. The residue was purified by thin layer chromatography. Solvent System E. The resulting oil was dissolved in ethyl acetate and treated with a solution of tartaric acid in ethyl acetate. The white precipitate was collected by filtration to give the title compound (0.326 g).

Nmr (CDCl$_3$): 2.5, t, (1H); 2.8 to 3, m, (3H) 5.4, s, (2H); 5.7 to 5.8, s+t, (4H); 6.4 to 6.5, s+t+m, (7H); 7.05, t, (2H); 7.7 to 8.5, m, (8H).

Found: C, 49.8; H, 6.3; N, 14.9; $C_{19}H_{28}N_6O_2.C_4H_6O_6.2H_2O$ requires: C, 49.5; H, 6.8; N, 15.0%.

The following compounds were similarly prepared from 1-methyl-5-[[3-[3-(1-piperidinylmethyl)phenoxy]-propyl]amino]-1H-1,2,4-triazole-3-propanoic acid (A), by the above method except that the excess thionyl chloride was removed under reduced pressure to leave a residue which was dissolved in dichloromethane (15 ml) before adding the appropriate amine.

(b) (A) (0.32 g) and dimethylamine (0.27 g) gave N,N,1-Trimethyl-5-[[3-[3-(1-piperidinyl)methyl]-phenoxy]propyl]amino-1H-1,2,4-triazole-3-propanamide (0.05 g) as a yellow solid, m.p. 62°–4°.

Found: C, 64.2; H, 8.5; N, 19.4; $C_{23}H_{26}N_6O_2$ requires: C, 64.4; H, 8.5; N, 19.6%.

(c) (A) (0.5 g) and pyrrolidine (0.2 g) gave 1-[3-[1-methyl-5-[[3-[3-(1-piperidinylmethyl)phenoxy]propyl]-amino]-1H-1,2,4-triazol-3-yl]-1-oxopropyl]pyrrolidine (0.13 g) as as a brick-red solid. T.l.c. System E Rf 0.5.

Nmr (CDCl$_3$): 2.74, m, (1H); 3.0–3.3, m, (3H); 5.4, t, (1H), 5.89, t, (2H); 6.2–6.6, m, (6H); 6.49, s, (3H); 6.53, s, (2H); 6.8–7.15, t, (2H); 7.15–7.4, t, (2H); 7.56, m, (4H); 7.7–8.3, m, (6H); 8.2–8.6, m, (6H).

EXAMPLE 9

N-[3-[3-(1-piperidinylmethyl)phenoxy]propyl]-3-(2-thienyl)-1H-1,2,4-triazole-5-amine hemi-hydrate A mixture of N-amino-N-[3-[3-(1-piperidinylmethyl)-phenoxy]propyl]guanidine hydrogen carbonate, hemihydrate (1.0 g) and 2-thiophene carbonyl chloride (0.63 g) in pyridine (5 ml) was stirred at 24° for 12 h and then heated under reflux for 3 h. The mixture was dissolved in water (50 ml), basified with potassium carbonate, washed with cyclohexane and extracted with ether and ethyl acetate. The combined organic extracts were evaporated to leave a brown gum (1.0 g) which was chromatographed using methanol as eluent, to give a solid (0.20 g). Recrystallisation of the solid from a mixture of light petroleum (b.p. 60°–80°) and methyl acetate gave the title compound as a white powder (0.12 g), m.p. 157°.

Nmr (CDCl$_3$) 2.5, m, (1H); 2.7–3.3, m, (6H); 4.7, t, (1H); 6.0, q, (2H); 6.55–6.65, q+s. (4H); 7.65–8.0, m, (6H); 8.5, m, (6H).

EXAMPLE 10

3-(3-Pyridylmethyl)-N-[3-[3-(1-piperidinylmethyl)-phenoxy]propyl]-1H-1,2,4-triazole-5-amine A solution of N-amino-N'-[3-[3-(1-piperidinylmethyl)phenoxy]propyl]guanidine hydroiodide hemitartrate (5 g) in water (50 ml) was basified with sodium hydroxide and extracted with ethyl acetate. The extract was evaporated to give a gum (2.33 g) which has heated at 150° for 12 h with 3-pyridylacetic acid hydrochloride (1.46 g). The mixture was dissolved in water (50 ml), basified with sodium hydroxide, washed with cyclohexane and extracted with ether. The ethereal extracts were dried and evaporated to leave a brown residue which was recrystallised from ethyl acetate to give the title compound as a cream crystalline solid (0.12 g), m.p. 126°–129°.

Nmr (CDCl$_3$): −2–0, br s, (1H); 1.4–1.6, m, (2H); 2.4, dd, (1H); 2.65–2.9, m+t, (2H); 3.0–3.3, m, (3H); 4.77, t, (1H); 6.1–6.13, t+s, (4H); 6.6–6.65, s+q, (4H); 7.6, m, (4H); 8.1, m, (2H); 8.5, m, (6H).

EXAMPLE 11

1-Methyl-N-[4-[3-(1-piperidinylmethyl)phenoxy]butyl]-3-trifluoromethyl-1H-1,2,4-triazole-5-amine N-[1-Methyl-3-trifluoromethyl-1H-1,2,4-triazol-5-yl]-4-[3-(1-piperidinylmethyl)phenoxy]butanamide A solution of 4-[3-(1-piperidinylmethyl)phenoxy]-butanoic acid (8.3 g), thionyl chloride (9 ml) and dimethylformamide (1 ml) in methylene chloride (250 ml) was stirred at 25° for 2 h. After evaporation the residue was dissolved in methylene chloride and 1-methyl-3-trifluoromethyl-1H-1,2,4-triazole-5-amine (5 g) was added and the mixture was stirred for 18 h at room temperature. The solution was evaporated, diluted with water, basified with sodium bicarbonate and extracted with ethyl acetate. The extract was dried and evaporated to give a brown oil which was extracted with hot diethyl ether. On standing the title compound (5.2 g) crystallised from the ether solution, m.p. 96°–97°.

Found: C, 56.8; H, 6.2; N, 16.1; F, 13.7; $C_{20}H_{26}F_3N_5O_2$ requires: C, 56.4; H, 6.2; N, 16.5; F, 13.4%.

1-Methyl-N-[4-[3-(1-piperidinylmethyl)phenoxy]butyl]-3-trifluoromethyl-1H-1,2,4-triazole-5-amine A suspension of the above butanamide (5 g) and lithium aluminium hydride (5 g) in dry tetrahydrofuran was stirred at room temperature for 18 h and then heated at reflux for 1 h. The suspension was treated with water and sodium hydroxide, filtered and evaporated to give white crystals which were recrystallised from hot ethyl acetate to give the title compound (1.1 g). m.p. 70°.

Found: C, 58.1, H, 6.9; N, 16.7; $C_{20}H_{28}F_3N_5O$ requires: C, 58.4; H, 6.9; N, 17.0%.

EXAMPLE 12

3-Methylsulphonyl-N-[4-[3-(1-piperidinylmethyl)-phenoxy]butyl]-1H-1,2,4-triazole-5-amine Peracetic acid (1.8 ml) in acetic acid (13 ml) was added at 0° to a solution of 3-methylthio-N-[4-[3-(1-piperidinylmethyl)phenoxy]butyl]-1H-1,2,4-triazole-5-amine (1.6 g) and sodium acetate (0.69 g) in acetic acid (22 ml) and the mixture was stirred at room temperature, for 18 h. Excess peracetic acid was decomposed with sodium sulphite (3.0 g) in water and the resulting suspension evaporated. The residue was neutralised with sodium bicarbonate solution and extracted with chloroform. The extract was evaporated to give an oil which was crystallised from methyl acetate-petroleum ether (5:1) to give the title compound as a beige powder (0.75 g), m.p. 79°–81°.

Found: C, 55.8; H, 7.1; N, 16.9; $C_{19}H_{29}N_5O_3S$ Requires: C, 56.0; H, 7.2; N, 17.2%.

EXAMPLE 13

(a)

1-Methyl-5-[[3-[3-(1-piperidinylmethyl)phenoxy]propyl]amino]-1H-1,2,4-triazole-3-carboxaldehyde oxime hemifumarate A solution of hydroxylamine hydrochloride (0.36 g) in ethanol (20 ml) was treated with potassium hydroxide (0.28 g). A solution of 1-methyl-5-[[3-[3-(1-piperidinylmethyl)phenoxy]propyl]amino]-1H-1,2,4-triazole-3-carboxaldehyde (A) (1.5 g) in ethanol (20 ml) was added. The mixture was stirred for 15 minutes and then filtered. The filtrate was evaporated and the residue was dissolved in chloroform and washed with water. The organic solution was dried, filtered and evaporated and the solid residue was dissolved in ethyl acetate/ethanol and treated with a solution of fumaric acid in ethyl acetate/ethanol, to give the title compound (0.05 g) m.p. 173°–4°.

Assay Found: C, 58.2; H, 7.0; N, 19.1; $C_{19}H_{28}N_6O_2.\frac{1}{2}C_4H_4O_4$ requires: C, 58.6; H, 7.0; N, 19.5%.

(b) Similarly prepared from A (0.5 g) and methoxyamine (0.14 g) was 1-methyl-5-[[3-[3-(1-piperidinylmethyl)phenoxy]propyl]amino]-1H-1,2,4-triazole-3-carboxaldehyde O-methyloxime (0.4 g). T.l.c. System B, Rf 0.7.

Nmr (CDCl$_3$): 2.03, s, (1H); 2.78, t, (1H); 3.0–3.3, m, (3H); 5.18, t, (1H); 5.90–6.02, t+s, (5H); 6.32–6.42, q+s, (5H): 6.58, s, (2H); 7.6–7.88, m, (6H); 8.5, m, (6H).

EXAMPLE 14

1-Methyl-5-[[3-[3-(1-piperidinylmethyl)phenoxy]propyl]amino]-1H-1,2,4-triazole-3-carbonitrile A solution of 1-methyl-5-[[3-[3-(1-piperidinylmethyl)phenoxy]propyl]amino]-1H-1,2,4-triazole-3-carboxaldehyde oxime (0.75 g) in acetic anhydride (4 ml) was heated at 100° for 10 hours. The mixture was poured onto aqueous sodium bicarbonate and extracted with toluene. The extract was dried (Na$_2$SO$_4$), filtered, and evaporated to give a solid, which was crystallized from diethyl ether and petroleum ether (b.p. 60°–80°) to give the title compound (0.3 g) as a white powder, m.p. 66°–7°.

Found: C, 64.2; H, 7.4; N, 23.3; $C_{19}H_{26}N_6O$ requires: C, 64.4; H, 7.4; N, 23.7%.

EXAMPLE 15

1-Methyl-3-methylsulphonylmethyl-N-[3-[3-(1-piperidinylmethyl)phenoxy]propyl]-1H-1,2,4-triazole-5-amine.

Peracetic acid (1.05 ml of a 6.1M solution) in acetic acid (7 ml) was added to an ice-cooled solution of 1-methyl-3-methylthiomethyl-N-[3-[3-(1-piperidinylmethyl)phenoxy]propyl]-1H-1,2,4-triazole-5-amine (0.82 g) in acetic acid (10 ml) with sodium acetate (0.52 g). The mixture was stirred at room temperature for 18 h, sodium sulphite (1.25 g) added and the mixture evaporated to dryness. The residue was basified to pH 8 with sodium bicarbonate solution, washed with ethyl acetate, basified to pH 10 with sodium carbonate and extracted with ethyl acetate to give a foam (0.46 g). This was crystallised from methyl acetate-petroleum ether (b.p. 60°–80°) to give the title compound as a white solid (0.22 g), m.p. 121°–122°.

Found: C, 57.0; H, 7.4; N, 16.5; $C_{20}H_{31}N_5O_3S$ requires: C, 57.0; H, 7.4; N, 16.6%.

EXAMPLE 16

N-[3-[3-[(Dimethylamino)methyl]phenoxy]propyl]-1-methyl-3-[(methylsulphonyl)methyl]-1H-1,2,4-triazol-5-amine Methyl 1-methyl-N-[(methylsulphonyl)acetyl]-2-(phenylmethylene)hydrazinecarboximidothioate (1.3 g) and 3-[3-[(dimethylamino)methyl]phenoxy]propanamine (0.81 g) were heated at 70° under water vacuum for 1 h. After cooling, the reaction mixture was dissolved in toluene (10 ml) and 5N hydrochloric acid (6 ml), and stirred at 20° during 18 h. The acidic layer was washed with toluene and basified (pH 10) with potassium carbonate. The mixture was then extracted with ethyl acetate to give the title compound (1.2 g) as an oil. T.l.c. System A Rf 0.39.

N.m.r. (CDCl$_3$): 2.71, t, (1H); 3.0–3.3, m, (3H); 5.4, t, (1H); 5.7–6.0, m, (4H); 6.35, t, (2H); 6.45, s, (3H); 6.63, s, (2H); 6.93, s, (3H); 7.74, s, (6H); 7.8, m, (2H).

EXAMPLE 17

(a)

N-Methyl-N'-[[1-methyl-5-[[3-[3-(1-piperidinylmethyl)phenoxy]propyl]amino]-1H-1,2,4-triazol-3-yl]methyl]-2-nitro-1,1-ethenediamine 1-Methyl-5-[[3-[3-(1-piperidinylmethyl)phenoxy]propyl]amino]-1H-1,2,4-triazole-3-methanamine (0.2 g) and methyl-N-methyl-2-nitroimidothioate (0.08 g) in water (2.5 ml) was stirred for 48 h at 22° under water vacuum. The reaction mixture was acidified with glacial acetic acid and washed with ethyl acetate. The aqueous layer was basified to pH9 with solid potassium carbonate and extracted with ethyl acetate to give an oil (0.13 g), which was chromatographed using methanol to give the title compound as a solidified lemon-yellow foam (0.065 g).

Nmr (CDCl$_3$): −0.5, m, (1H); 2.1, m, (1H); 2.80, t, (1H); 3.0–3.3, m, (3H); 3.48, brs, (1H); ca 4.5, m, (1H); 5.78, brd, (2H); 5.98, t, (2H); 6.48, s+m, (5H); 6.63, s, (2H); 7.20, br, (2H); 7.67, m, (4H); 7.93, m, (2H); 8.6, m, (6H).

Ir (CHBr$_3$): 2805 cm$^{-1}$, 2760, 2725, 1385, 760.

(b) Similarly prepared from 1-methyl-5-[[3-[3-(1-piperidinylmethyl)phenoxy]propyl]amino]-1H-1,2,4-triazole-3-propanamine (0.46 g) and methyl N-methyl-2-nitroimidothioate (0.27 g) was N-methyl-N'-[3-[1-methyl-5-[[3-[3-(1-piperidinylmethyl)phenoxy]propyl]amino]-1H-1,2,4-triazol-3-yl]propyl]-2-nitro-1,1-ethenediamine as a gum (0.47 g). T.l.c. System C, Rf 0.34.

Nmr (CDCl$_3$): −0.4, m, (1H); 1, 9, m, (1H); 2.75–3.3, m, (4H); 3.38, s, (1H); 4.9, m, (1H); 5.87, t, (2H); 6.3–6.6, m, (9H); 7.1–8.2, m, (13H); 8.3–8.6, m, (6H).

EXAMPLE 18

3-[1-Methyl-5-[[3-[3-(1-piperidinylmethyl)phenoxy]propyl]amino]-1H-1,2,4-triazol-3-yl]-2-propenoic acid hydrate (1:2.5)

A solution of 1-methyl-5-[[3-[3-(1-piperidinylmethyl)phenoxy]propyl]amino]-1H-1,2,4-triazole-3-carboxaldehyde (0.8 g), malonic acid (0.23 g), piperidine (0.05 ml) and pyridine (5 ml) was heated at 90° for 4 h. The resulting solution was azeotroped with toluene to give a brown foam (0.9 g) which was partitioned between aqueous sodium hydroxide and diethyl ether. The aqueous layer was acidified (pH 5.5) to precipitate the title compound (0.4 g) as a white solid, m.p. 95°–100° [decomp].

Found: C, 56.7; H, 8.0; N, 15.5; $C_{21}H_{29}N_5O_3.2.5H_2O$ requires: C, 56.7; H, 7.7; N, 15.8%.

EXAMPLE 19

3-[1-Methyl-5-[[3-[3-(1-piperidinylmethyl)phenoxy]propyl]amino]-1H-1,2,4-triazol-3-yl]-3-propanol Ethyl 3-[1-methyl-5-[[3-[3-(1-piperidinylmethyl)phenoxy]propyl]amino]-1H-1,2,4-triazol-3-yl]-2-propenoate A solution of 3-[1-methyl-5-[[3-[3-(1-piperidinylmethyl)phenoxy]propyl]amino]-1H-1,2,4-triazol-3-yl]-2-propenoic acid (0.8 g) and concentrated hydrochloric acid (1 ml) in ethanol was stirred 60° for 18 h, followed by 6 h at reflux. Sodium carbonate (5 g) was added and the reaction mixture was evaporated in vacuo to give an off-white solid which was partitioned between sodium carbonate solution and chloroform. The organic phase was evaporated to give the title compound as a brown gum (0.85 g). T.l.c. System C, Rf 0.66.

Nmr (CDCl$_3$): 2.46, d, (1H); 2.69, t, (1H); 2.93–3.28, 3.23, m+d, (4H); 5.43, t, (1H); 5.58–5.9, m, (4H); 6.32–6.38, q+s (5H); 6.52, s, (2H); 7.55, m, (2H); 7.80, m, (2H); 8.44–8.68, m+t, (9H).

3-[1-methyl-5-[[3-[3-(1-piperidinylmethyl)phenoxy]propyl]amino]-1H-1,2,4-triazol-3-yl]-2-propenol A stirred solution the the above 2-propenoate (0.8 g) in tetrahydrofuran at 0° under nitrogen was treated with aluminium hydride solution (0.3M; 6.2 ml) for 4 h. The reaction mixture was quenched with water and filtered through hyflo. The residue was washed with tetrahydrofuran and the combined filtrate evaporated to leave a brown oil which was chromatographed using dichloroethane:ethanol:0.88 ammonia (60:8:1) to give the title compound (0.1 g) contaminated with the corresponding 3-hydroxypropyl triazole as a brown gum. T.l.c. System C, Rf 0.12.

Nmr (CDCl$_3$): 2.7, t; 3.0–3.2, m; 3.22, dt; 3,55, d: 5.15, t; 5.72, d; 5.9, m; 6.3, q; 6.5, s; 6.52, s; 7.55, m; 7.85, m; 8.45, m; contaminant peaks: 6.4, t; 7.3, t; 8.0, m.

EXAMPLE 20

1-[1-Methyl-5-[[3-[3-(1-piperidinylmethyl)phenoxy]propyl]amino]-1H-1,2,4-triazol-3-yl]ethanone α,1-Dimethyl-5-[[3-[3-(1-piperidinylmethyl)phenoxy]propyl]amino]-1H-1,2,4-triazole-3-methanol A mixture of 3-[3-[1-(piperidinylmethyl)]phenoxy]propanamine (1.8 g) and methyl N-[2-(acetyloxy-1-oxypropyl)-1-methyl-2-(phenylmethylene)]hydrazinecarboximidothioate (2.3 g) was heated at 60°–70° for 1 hour. The mixture was dissolved in toluene (50 ml) and 2N hydrochloric acid (15 ml) was added. The mixture was stirred for 18 h and heated at 80° for 40 minutes. The mixture was neutralized with sodium bicarbonate and washed with toluene. The aqueous solution was basified with aqueous sodium hydroxide and extracted with ethyl acetate. The extract was dried, filtered and evaporated to give a solid residue, which was crystallized from diethyl ether and petroleum ether (b.p. 60°–80°) to give the title compound (1.2 g) as a white solid. m.p. 67°–68°.

1-[1-Methyl-5-[[3-[3-(1-piperidinylmethyl)phenoxy]propyl]amino]-1H-1,2,4-triazol-3-yl]ethanone Activated manganese dioxide (9 g) was added to a stirred solution of the above α-methylmethanol (0.5 g) in dichloromethane (10 ml). After 48 hours the mixture was filtered through hyflo and the filtrate evaporated to give the title compound (0.073 g) as a colourless oil. T.l.c. System A, Rf 0.7.

Nmr (CDCl$_3$): 2.77, t, (1H); 3.0–3.3, m, (3H); 5.02, t, (1H), 5.90, t, (2H); 6.37, s+m, (5H); 6.58, s, (2H); 7.45, s, (3H); 7.6, m, (4H); 7.88, m, (2H);, 8.3–8.7, m, (6H).

EXAMPLE 21

N-[[1-Methyl-5-[[3-[3-(1-piperidinylmethyl)phenoxy]propyl]amino]-1H-1,2,4-triazol-3-yl]methyl]-N'-phenyl urea A mixture of 1-methyl-5-[[3-[3-(1-piperidinylmethyl)phenoxy]propyl]amino]-1H-1,2,4-triazole-3-methanamine (0.75 g) and phenyl isocyanate (0.25 ml) in dry acetonitrile was stirred at 30° for 3 h. The solvent was removed in vacuo and the solid residue was crystallized from methyl acetate and petroleum ether (b.p. 60°–80°) to give the title compound (0.94 g) as a white solid, m.p. 120°–1°. T.l.c. System A, Rf 0.6.

EXAMPLE 22

N-Cyano-N'-methyl-N''-[[1-methyl-5-[[3-[3-(1-piperidinylmethyl)phenoxy]propyl]amino]-1H-1,2,4-triazol-3-yl]methyl]guanidine A solution of 1-methyl-5-[[3-[3-(1-piperidinylmethyl)phenoxy]propyl]amino]-1H-1,2,4-triazole-3-methanamine (1.0 g) in diethylether (20 ml) was added to a refluxing solution of N-cyanocarbimidothioic acid dimethyl ester (0.45 g) in ether (50 ml) and the mixture heated at reflux for 8 h. After cooling, a colourless solid (0.65 g) precipitated and was collected by filtration, m.p. 121°–122°. This material was added to a solution of methylamine (33% in ethanol, 10 ml) in ethanol (50 ml) and the solution heated at reflux for 16 h. The mixture was evaporated to give a solid which was recrystallized from ethyl acetate to give the title compound as a colourless solid (0.34 g), m.p. 138°–139°.

Nmr (CDCl$_3$): 2.73, t, (1H); 2.8–3.3, m (4H); 3.93, t, (1H); 5.0, t, (1H); 5.8, d, (2H); 5.9, t, (2H); 6.45, q, (2H); 6.48, s, (3H); 6.58, s, (2H); 7.16, d, (3H); 7.65, m, (4H); 7.9, m, (2H); 8.5, m, (6H).

EXAMPLE 23

N-[[1-Methyl-5-[[3-[3-(1-piperidinylmethyl)phenoxy]propyl]amino]-1H-1,2,4-triazol-3-yl]methyl]benzamide 50% Benzoic anhydride (0.57 g) was added to a solution of 1-methyl-5-[[3-[3-(1-piperidinylmethyl)phenoxy]propyl]amino]-1H-1,2,4-triazole-3-methanamine (0.4 g) in pyridine (10 ml) and stirred for 0.5 h at 80°. Excess pyridine was evaporated and the residue was diluted with water (50 ml), basified with solid potassium carbonate and extracted with ethyl acetate. The extract was evaporated to give a gum which was chromatographed using methanol. The resulting oil was crystallized from ethyl acetate-petroleum ether (b.p. 60°–80°) (1:2) to give the title compound (0.26 g) as white crystals, m.p. 70°.

Found: C, 65.6; H, 7.3; N, 17.6; $C_{26}H_{34}N_6O_2$ requires: C, 65.6; H, 7.5; N, 17.7%.

EXAMPLE 24

(a)

N-[[1-Methyl-5-[[3-[3-(1-piperidinylmethyl)phenoxy]-propyl]amino]-1H-1,2,4-triazol-3-yl]methyl]methanesulphonamide A solution of 1-methyl-5-[[3-[3-(1-piperidinylmethyl)-phenoxy]propyl]amino]-1H-1,2,4-triazole-3-methanamine (0.5 g) and methane sulphonyl chloride (0.16 g) in pyridine (25 ml) was stirred at room temperature for 18 h. The solution was evaporated to give a brown oil which was crystallised from a mixture of ethyl acetate and petroleum ether (b.p. 60°–80°) to give the title compound (0.14 g) as a white powder, m.p. 117°–118°.

Found: C, 55.1; H, 7.4; N, 18.8; $C_{20}H_{32}N_6O_3S$ requires: C, 55.0; H, 7.4; N, 19.2%.

The following compounds were similarly prepared from the appropriate 3-aminoalkyl-triazole:

(b) 1-methyl-5-[[3-[3-(1-piperidinylmethyl)phenoxy]-propyl]amino]-1H-1,2,4-triazole-3-propanamine (0.46 g) and methane sulphonyl chloride (0.11 ml) gave N-[3-[1-methyl-5-[[3-[3-(1-piperidinylmethyl)phenoxy]propyl]amino]-1H-1,2,4-triazol-3-yl]propyl]methanesulphonamide as a gum (0.26 g). T.l.c. Sytem C, Rf 0.35.

Nmr ($CDCl_3$): 2.7–3.3, m, (4H); 3.45, t, (1H); 5.40, t, (1H); 5.88, t, (2H); 6.2–6.7, m, (9H); 6.79, q, (2H); 7.10, s, (3H); 7.32, t, (2H); 7.6–8.5, m, (10H).

(c) 1-methyl-5-[2-[[2-[3-(1-piperidinylmethyl)phenoxy]ethoxy]ethyl]amino]-1H-1,2,4-triazole-3-methanamine (0.8 g) and methane sulphonyl chloride (0.25 g) gave N-[[1-methyl-5-[2-[[2-[3-(1-piperidinylmethyl)-phenoxy]ethoxy]ethyl]amino]-1H-1,2,4-triazol-3-yl]methyl]methanesulphonamide (0.6 g) as a pale brown oil. T.l.c. System B, Rf 0.4.

Nmr ($CDCl_3$) 2.77, t, (1H); 3.0–3.3, m, (3H); 4.55 br.t, (1H); 5.45, t, (1H); 5.8, s, (2H); 5.9–6.2, m, (4H); 6.33, t, (2H); 6.45, q, (2H); 6.58, 2×s, (5H); 7.06, s, (3H); 7.65, m, (4H); 8.5, m, (6H).

EXAMPLE 25

(a)

5-[[3-[3-[(Dimethylamino)methyl]phenoxy]propyl]-amino]-1-methyl-1H-1,2,4-triazole-3-carboxaldehyde fumarate 5-[[3-[3-[(dimethylamino)methyl]phenoxy]propyl]-amino]-1-methyl-1H-1,2,4-triazole-3-methanol (2.12 g) and activated manganese dioxide (6.32 g) were stirred together in chloroform (40 ml) for 4 h at 24°. The mixture was filtered, and the filtrate evaporated to give a gum which was chromatographed on "florisil" using ethanol:ethyl acetate (1:9). The resulting oil was dissolved in ethyl acetate/ethanol and added to a solution of fumaric acid in ethyl acetate/ethanol to give the title compound (0.71 g) as a white solid, m.p. 133°–135°.

Nmr ($D_2O$); 0.50, s, (1H); 2.63, t, (1H); 2.75–3.05, m, (3H); 3.3, s, (2H); 5.76, m, (4H); 6.31–6.33, s+q, (5H); 7.18, s, (6H); 7.90, t, (2H).

(b) Similarly prepared from 5-[2-[[[5-(dimethylamino)methyl]-4-methyl-2-furanylmethyl]thio]-ethyl]amino]-1-methyl-1H-1,2,4-triazole-3-methanol (0.8 g) and activated manganese dioxide (6.0 g) in chloroform (40 ml) after 6 h at 24° was 5-[2-[[5-[(dimethylamino)methyl]-4-methyl-2-furanylmethyl]thio]-ethyl]amino]-1-methyl-1H-1,2,4-triazole-3-carboxaldehyde fumarate (0.4 g) m.p. 149°–151°.

Nmr ($D_2O$): 0.3, s, (1H); 3.29, s, (2H); 4.05, s, (1H); 5.7, s, (2H); 6.20, s, (2H); 6.3, s, (2H) 6.45, m, (3H); 7.10–7.25, t+s, (8H); 7.95, s, (3H).

EXAMPLE 26

1-Methyl-3-(methylsulphonyl)methyl-N-[3-[4-(1-piperidinylmethyl)phenoxy]propyl]-1H-1,2,4-triazole-5-amine 1-Methyl-3-(methylthio)methyl-N-[3-[4-(1-piperidinylmethyl)phenoxy]propyl]-1H-1,2,4-triazole-5-amine Methyl N-[2-(methylthio)acetyl]-1-methyl-2-(phenylmethylene)hydrazine carboximidothioate (1.2 g) and 3-[4-(1-piperidinylmethyl)phenoxy]propanamine (0.9 g) were heated at 55° under water vacuum for 2 h. Additional carboximidothioate (0.09 g) was then added and the mixture heated for a further 1 h. The reaction mixture was dissolved in toluene (5 ml) and 5N hydrochloric acid (4 ml), stirred at room temperature for 18 h and the phases separated. The aqueous phase was basified to pH 10 with sodium carbonate and extracted with ethyl acetate to give an oil, which was chromatographed using ethyl acetate-methanol (3:1) to give the title compound (1.04 g) as an orange brown oil.

Nmr ($CDCl_3$): 2.72, m, (2H); 3.13, m, (2H); 5.56, t, (1H); 5.87, t, (2H); 6.36, q, (2H); 6.42, s, (2H); 6.42, s, (2H); 6.48, s, (3H); 6.56, s, (2H); 7.60, m, (4H); 7.82, s, (3H); 7.84, m, (2H); 8.2–8.8, m, (6H).

Ir ($CHBr_3$): 3400 $cm^{-1}$, 2790, 2745, 2710, 1583, 1523.

1-Methyl-3-(methylsulphonyl)methyl-N-[3-[4-(1-piperidinylmethyl)phenoxy]-propyl]-1H-1,2,4-triazole-5-amine Peracetic acid (0.9 ml, 6.1M) in acetic acid (5 ml) was added at 0° to a solution of the above 3-(methylthio)methyl-triazole (0.69 g) and the mixture was stirred at room temperature for 18 h. Excess peracetic acid was decomposed with sodium sulphite (1 g) in water and the mixture was evaporated. The residue was basified with sodium bicarbonate solution and extracted with chloroform. The extract was evaporated to give a white solid which was recrystallized from methyl acetate-petroleum ether to give the title compound (230 mg) as a white solid, m.p. 131°–4°.

Nmr ($CDCl_3$): 2.70, d, (2H); 3.13, d, (2H); 5.40, t, (1H); 5.80, s, (2H); 5.90, t, (2H); 6.35, dt, (2H), 6.45, s, (3H); 6.55, s, (2H); 6.90, s, (3H); 7.60, m, (4H); 7.81, m, (2H); 8.2–8.8, m, (6H).

EXAMPLE 27

N-[[5-[[2-[[5-[(Dimethylamino)methyl]-2-furanylmethyl]thio]ethyl]amino]-1-methyl-1H-1,2,4-triazol-3-yl]methyl]methanesulphonamide A solution of 5-[[2-[[5-[(Dimethylamino)methyl]-2-furanylmethyl]thio]ethyl]amino]-1-methyl-1H-1,2,4-triazole-3-methanamine (0.65 g) and methane suphonyl chloride (0.17 ml) in pyridine (5 ml) was stirred at room temperature for 18 h. The pyridine solution was decanted off to leave a dark red oil which was treated with saturated sodium carbonate solution (25 ml) and extracted with ethyl acetate to give the title compound (0.07 g) as a pale brown oil. T.l.c. System A, Rf 0.5.

Nmr ($CDCl_3$) 3.90, s, (2H); 5.22, brt, (1H); 5.80, s, (2H); 6.30, s, (2H); 6.48, s, (3H); 6.55, q, (2H); 6.60, s, (2H); 7.03, s, (3H); 7.76, s, (6H).

EXAMPLE 28

N-[[5-[[3-[3-[(Dimethylamino)methyl]phenoxy]propyl]amino]-1-methyl-1H-1,2,4-triazol-3-yl]methyl]methanesulphonamide A mixture of 5-[[3-[3-[(Dimethylamino)methyl]phenoxy]propyl]amino]-1-methyl-1H-1,2,4-triazole-3-methanamine (0.75 g) and methane sulphonyl chloride (0.18 ml) in dry pyridine (15 ml) was stirred at room temperature for 18 hours. The solvent was removed in vacuo and the residue was dissolved in aqueous sodium carbonate and extracted with ethyl acetate. The organic solution was evaporated leaving the title compound (0.5 g). T.l.c. System B, Rf 0.6.

Nmr (CDCl$_3$): 2.8–2.9, t, (1H); 3.1–3.25, m, (3H); 3.9, brs., (1N); 4.55, t, (1H); 5.7–6.00, s+t, (4H); 6.3–6.7, m+s+s, (7H); 7.10, s, (3H); 7.75–8.0, s+m, (8H).

EXAMPLE 29

(a)

N-[3-[3-[[(2-Furanylmethyl)amino]methyl]phenoxy]propyl]-1-methyl-3-[(phenylsulphonyl)methyl]-1H,1,2,4-triazol-5-amine A solution of 3-[3-[[1-Methyl-3-[(phenylsulphonyl)methyl]-1H-1,2,4-triazol-5-yl]amino]propoxy]benzaldehyde (A), (1.5 g) in ethanol (50 ml) was treated with furfurylamine (7.5 ml) at room temperature for 1.5 h. The solution was treated with sodium borohydride (2.0 g) and the suspension stirred for 18 h at room temperature. The mixure was quenched with water, partially evaporated and extracted with ethyl acetate to give a red oil which was purfified by column chromatography using methanol:ethyl acetate (1:4) to give the title compound as a yellow oil (1.2 g). T.l.c. methanol:ethyl acetate (1:4), Rf 0.4.

Nmr (CDCl$_3$): 2.10, m, (2H); 2.3–2.8, m, (5H); 3.0–3.3, m, (3H); 3.7–3.9, m, (2H); 5.48, t, (1H); 5.65, s, (2H); 5.93, t, (2H); 6.22, s, (4H); 6.50, s+q, (5H); 7.95, m, (2H); 8.10, s, (1H).

(b) Similarly prepared from A (1.5 g) and hexylamine (7.5 ml) was N-[3-[3-[(hexylamino)methyl]phenoxy]propyl]-1-methyl-3-[(phenylsulphonyl)methyl]-1H-1,2,4-triazol-5-amine (1.3 g) as a red oil. T.l.c. methanol:ethyl acetate (1:1), Rf 0.8.

Nmr (CDCl$_3$): 2.10, m, (2H); 2.2–2.9, m, (4H); 3.0–3.3, m, (3H); 5.43, t, (1H); 5.69, s, (2H); 5.95, t, (2H); 6.25, s, (2H); 6.43, s+q, (5H); 7.3–7.5, t+s, (4H); 7.98, m, (2H); 8.3–9.0, m, (8H); 9.13, t, (3H).

EXAMPLE 30

(a) Ethyl 1-methyl-5-[[3-[3-(1-piperidinylmethyl)phenoxy]propyl]amino]-1H-1,2,4-triazole-3-acetate salt wih tartaric acid (1:1)

Ethyl 3-[[[1-methyl-2-(phenylmethylene)hydrazino][[3-[3-(1-piperidinylmethyl)phenoxy]propyl]amino]methylene]amino]-3-oxopropanoate A mixture of 3-[3-(1-piperidinylmethyl)phenoxy]propanamine (A) (3.61 g) and ethyl 3-[[[1-methyl-2-(phenylmethylene)hydrazino](methylthio)methylene]amino]-3-oxopropanoate (4.7 g) was heated at 50° under water pump vacuum during 4 h. to gave the title compound as an orange gum (7.3 g). T.l.c. System D, R$_f$ 0.65.

Ethyl 1-methyl-5-[[3-[3-(1-piperidinylmethyl)phenoxy]propyl]amino]-1H-1,2,4-triazole-3-acetate salt with tartaric acid (1:1)

A solution of the above 3-oxopropanoate (1.84 g) in ethanol (50 ml) and 2N hydrochloric acid (7 ml), was heated under reflux during 4 h. The cool soluion was washed with ethyl acetate (50 ml). The aqueous layer was basified to pH 9 with potassium carbonate and extracted with ethyl acetate (3×50 ml). The solvent was evaporated to leave a pale yellow oil (0.6 g) which was purified by column chromatography using methanol to give a yellow a pale yellow oil (0.47 g). This oil was dissolved in ethyl acetate (10 ml) and treated with a solution of d-tartaric acid (30 mg) in ethyl acetate (100 ml) to give the title compound (60 mg) as a white powder, m.p. 65° (softens).

Nmr (CDCl$_3$), free base: 2.77, t, (1H); 3–3.3, m, (3H); 5.4, t, (1H); 5.8, q, (2H); 5.9, t, (2H); 6.3–6.6, 3×s+q, (9H); 7.6, m, (4H); 7.85, m, (2H); 8.5, m, (6H); 8.72, t, (3H).

(b) Similarly prepared from ethyl-4-[[[1-methyl-2-(phenylmethylene)hydrazino](methylthio)methylene]amino]-4-oxobutanoate (9.0 g) and A (6.5 g) was 1-methyl-5-[[3-[3-(1-piperidinylmethyl)phenoxy]propyl]amino]-1H-1,2,4-triazole-3-propanoic acid (A) (3.7 g). T.l.c. methanol: Rf 0.3.

Nmr (CDCl$_3$): 2.75–3.0, m, (2H); 3.05–3.3, m, (2H); 4.95, m, (1H); 5.97, t, (2H); 6.3, s, (2H); 6.2–6.7, q, (2H); 6.55, s, (3H); 7.0–7.65 m, (8H); 7.92, m, (2H); 8.15–8.7, m, (6H).

EXAMPLE 31

1-Methyl-5-[[3-[3-(1-piperidinylmethyl)phenoxy]propyl]amino]-1H-1,2,4-triazole-3-acetic acid hydrate Ethyl 3[[[1-methyl-2-(phenylmethylene)hydrazine][[3-[3-(1-piperidinylmethyl)phenoxy]propyl]amino]methylene]amino]-3-oxo-propanoate (5.77 g) was dissolved in toluene (10 ml) and 5N hydrochloric acid (12 ml) and stirred at 25° for 18 h. The phases were separated and the aqueous layer basified to pH 10 with sodium carbonate solution, washed with ethyl acetate and evaporated to dryness. The solid residue was extracted with chloroform (4×50 ml) to give an oil (1.8 g) which was chromatographed using 2:3 ethyl acetate:methanol to give a foam which was triturated with ether to give the title compound (0.4 g) as a white solid.

Found: C, 59.5; H, 7.6; N, 16.8; C$_{20}$H$_{29}$N$_5$O$_3$.H$_2$O requires: C, 59.2; H, 7.7; N, 17.3%.

Nmr (D$_2$O): 2.55, dd, (1H); 2.8–3.0, m, (3H); 5.80, t, (2H); 5.92, s, (2H); 6.46, s, (3H); 6.46, m, (2H); 6.57, s, (2H); 6.8–7.05, m, (4H); 7.87, m, (2H); 8.0–8.5, m, (6H).

EXAMPLE 32

3-(Chloromethyl)-1-methyl-N-[4-[3-(1-piperidinylmethyl)phenoxy]butyl]-1H-1,2,4-triazole-5-amine A mixture of 1-methyl-5-[4-[3-(1-piperidinylmethyl)phenoxy]butyl]amino-1H-1,2,4-triazole-3-methanol (0.75 g) and thionyl chloride (4 ml) was stirred at room temperature for 2 h. The mixture was evaporated in vacuo and the residue was dissolved in chloroform and washed with sodium bicarbonate. The organic extract was dried and evaporated to give the title compound as an oil (0.75 g) T.l.c. System E R$_f$0.65.

NMR (CDCl$_3$): 2.76, t, (1H); 3.0–3.3, m, (3H); 5.53, s, (2H); 5.7–6.0, t+m, (3H); 6.5–6.6, s+s+m, (7H); 7.65, m, (4H); 8.0–8.3, m, (4H); 8.3–8.6, m, (6H).

EXAMPLE 33

N-[2-[[[5-[(Dimethylamino)methyl]-2-furanyl]methyl]-thio]ethyl]-1-methyl-3-[(methylsulphonyl)methyl]-1H-1,2,4-triazol-5-amine Methyl 1-methyl-N-[(methylsulphonyl)acetyl]-2-(phenylmethylene)hydrazinecarboximidothioate (1.05 g) and 5-[[2-aminoethyl)thio]methyl]-N,N-dimethyl-furanmethanamine (0.85 g)in acetonitrile (3 ml) were heated on a steam bath at atmospheric pressure for 5 minutes then under water vacuum for 10 minutes. The oily residue was dissolved in acetonitrile (3 ml) and the solution re-evaporated under water vacuum. The oily residue was dissolved in 2N hydrochloric acid (3 ml) and 5N hydrochloric acid (4 ml) added to the solution. The solution was heated on a steam bath for 15 minutes and after cooling to room temperature, water (10 ml) was added and the oily suspension extracted with ethyl acetate. The aqueous phase was basified with sodium carbonate and the oily suspension extracted with ethyl acetate to yield an oil (0.84 g). This was chromatographed (using solvent system D) to give the title compound (0.78 g) as an oil. T.l.c. System D, Rf 0.5.

Nmr. (CDCl$_3$) 3.85, s, (2H); 5.20, brt, (1H); 5.78, s, (2H); 6.28, s, (2H); 6.45, s, 6.52, q, 6.58, s, (7H); 6.90, s, (3H), 7.21, t, (2H), 7.73, s, (6H).

EXAMPLE 34

1-Methyl-5-[[3-[3-(1-piperidinylmethyl)phenoxy]-propyl]amino]-1H-1,2,4-triazole-3-acetonitrile A solution of 1-methyl-5-[[3-[3-(1-piperidinylmethyl)-phenoxy]propyl]amino]-1H-1,2,4-triazole-3-methanol (3.6 g) in dry dichloromethane was treated with methane sulphonyl chloride (0.85 ml) at 0° for 3 h, poured into sodium carbonate solution (2M; 50 ml), and extracted with dichloromethane. The extract was washed with sodium hydroxide, water and brine and evaporated to give a white foam (4 g). This foam was dissolved in dimethylformamide (80 ml) and potassium cyanide (0.65 g) was added. The mixture was stirred at room temperature for 2 h and then at 65° for 24 h, cooled, concentrated, poured into sodium carbonate solution (2M; 100 ml) and extracted with ethyl acetate. The extract was washed with water and brine and evaporated to leave a brown oil (1.5 g) which was chromatographed using dichloromethane:ethanol:0.88 ammonia (60:8:0.5) to give the title compound as a brown gum (0.5 g). T.l.c. System C Rf 0.6.

Nmr (CDCl$_3$): 2.57, 3.0–3.3, m, (3H); 5.48, brt, (1H); 5.90, t, (2H); 6.2–6.6, 3×s+q, (9H); 7.6–7.9, m, (6H); 8.5, m, (6H).

Examples of Pharmaceutical compositions according to the invention are as follows:

| (a) TABLETS | | |
|---|---|---|
| | mg/tablet | mg/tablet |
| Active ingredient | 20.0 | 40.0 |
| Microcrystalline cellulose BPC | 99.5 | 199.0 |
| Magnesium stearate B.P. | 0.5 | 1.0 |
| Compression weight | 120.0 | 240.0 |

The drug is sieved through a 250 μm sieve, blended with the excipients and compressed using 6.5 mm and 8.0 mm diameter punches for the 20 and 40 mg strengths respectively. Tablets of other strengths may be prepared by increasing the compression weight and using punches to suit.

The tablets may be film coated with suitable film forming materials, e.g. methyl cellulose, ethyl cellulose or hydroxypropylmethyl cellulose, using standard techniques. Alternatively the tablets may be sugar coated.

| (b) CAPSULES | |
|---|---|
| | mg/capsule |
| Active ingredient | 20.0 |
| **Sta-Rx 1500 Starch | 79.5 |
| Magnesium Stearate B.P. | 0.5 |
| Fill weight | 100.0 |

**A form of directly compressible starch supplied by Colorcon Ltd. Orpington, Kent.

The active ingredient is seived through a 250 μm sieve and blended with other materials. The mix is filled into No. 3. hard gelatin capsules using a suitable filling machine. Other doses may be prepared by increasing the fill weight and if necessary changing the capsule size to accomodate the increase.

| (c) SUSTAINED RELEASE TABLETS | |
|---|---|
| | mg/tablet |
| Active ingredient | 80 |
| *Cutina HR | 25 |
| Lactose B.P. | 142.5 |
| Magnesium stearate B.P. | 2.5 |
| Compression weight | 250.0 |

*Cutina HR is a grade of microfine hydrogenated castor oil supplied by Sipon Products Ltd., London.

The drug is sieved through a 250 μm sieve and blended with the Cutina HR and lactose. The mixed powders are moistened with Industrial Methylated Spirits 74 O.P., granules are made, dried, screened and blended with the magnesium stearate. The lubricated granules are compressed using 8.5 mm punches to produce tablets with a hardness of not less than 10 Kp (Schleuniger tester).

| (d) INJECTION FOR INTRAVENOUS ADMINISTRATION | |
|---|---|
| | % w/v |
| Active ingredient | 0.25 |
| Water for Injections BP to | 100.00 |

Sodium chloride may be added to adjust the tonicity of the solution and the pH may be adjusted to that of maximum stability using either dilute acid or alkali.

The solution is prepared, clarified and filled under nitrogen into appropriate sized ampoules sealed by fusion of the glass. The injection is sterilised by heating in an autoclave using one of the acceptable cycles. Alternatively the solution may be sterilised by filtration and filled into sterile ampoules under aseptic conditions.

| (e) SYRUP | |
|---|---|
| | mg/5 ml dose |
| Active ingredient | 20.0 mg |
| Sucrose | 2750.0 mg |
| Glycerine | 500.0 mg |

-continued

(e) SYRUP

| | | mg/5 ml dose |
|---|---|---|
| Buffer | | 5 |
| Flavour | as necessary | |
| Colour | | |
| Preservative | | |
| Distilled water to | | 5.0 ml |

The active ingredient, buffer, flavour, preservative and colour are dissolved in some of the water. The remainder of the water is heated to approximately 80° C. and the sucrose is dissolved in this and cooled. The two solutions are mixed, adjusted to volume and clarified by filtration.

We claim:

1. A compound of the formula (I)

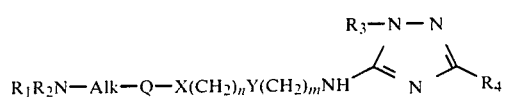

and physiologically acceptable salts and hydrates thereof, in which $R_1$ represents hydrogen, $C_{1-14}$ alkyl, $C_{3-8}$ cycloalkyl, $C_{3-6}$ alkenyl, $C_{3-6}$ alkynyl, ar $C_{1-6}$ alkyl, heteroaralkyl, trifluro $C_{1-6}$ alkyl or $C_{1-6}$ alkyl substituted by hydroxy, $C_{1-6}$ alkoxy, amino, $C_{1-6}$ alkylamino, di $C_{1-6}$ alkylamino or $C_{3-8}$ cycloalkyl; and $R_2$ represents hydrogen or $C_{1-4}$ alkyl; or $R_1$ and $R_2$ may together with the nitrogen atom to which they are attached form a pyrrolidino, piperidino, hexamethylenimino or tetrahydropyridino group which may be unsubstituted or may be substituted by one or more $C_{1-3}$ alkyl groups or a hydroxy group;

Alk represents a straight or branched alkylene chain of 1 to 6 carbon atoms;

Q represents a furan or thiophen ring in which incorporation into the rest of the molecule is through bonds at the 2- and 5-positions, the furan or thiophen ring optionally bearing a further substituent $R_5$ adjacent to the group $R_1R_2N$—Alk—; or Q represents a thiophen ring in which incorporation into the rest of the molecule is through bonds at the 2- and 4-positions, the thiophen ring optionally bearing a further substituent $R_5$ adjacent to the group $R_1R_2N$—Alk with the proviso that when the group $R_1R_2N$—Alk is in the 4-position then the group $R_5$ is in the 5-position; or Q represents a benzene ring in which incorporation into the rest of the molecule is through bonds at the 1- and 3- or 1- and 4-positions;

$R_5$ represents halogen or $C_{1-4}$ alkyl which may be substituted by hydroxy or $C_{1-4}$ alkoxy;

X represents oxygen, sulphur, —NH—, methylene or a bond;

Y represents oxygen, sulphur, methylene or a bond;

n represents zero, 1, 2 or 3, and m is an integer from 2 to 5, with the provisos that (a) the total number of atoms in the chain $X(CH_2)_nY(CH_2)_m$ is an integer from 3 to 8, (b) when X and Y represent oxygen or sulphur then n is 2 or 3, and (c) when X represents —NH— then Q is a benzene ring and Y represents methylene or a bond;

$R_3$ represents hydrogen, $C_{1-6}$ alkyl, $C_{3-6}$ alkenyl, ar $C_{1-6}$ alkyl or $C_{2-6}$ alkyl substituted by hydroxy or $C_{1-6}$ alkoxy;

$R_4$ represents the group $(CH_2)_pCH=CHR_6$ or $(CH_2)_qR_7$ where p is zero, 1 or 2 and q is zero, 1, 2, 3, 4, 5 or 6 and the alkylene chain $(CH_2)_q$ may be straight or branched, and $R_6$ is hydroxymethyl, 1H-tetrazol-5-yl, cyano, or the group $CH_2NHCOR_{17}$ or $CH_2NHSO_2R_{17}$ where $R_{17}$ is $C_{1-6}$ alkyl; or the group $COR_{19}$ where $R_{19}$ is hydrogen, hydroxyl, $C_{1-6}$ alkyl, $C_{1-6}$ alkoxy, amino, $C_{1-6}$ alkylamino or di $C_{1-6}$ alkylamino; or the group $CR_{19}{}^a=NR_{20}$ where $R_{19}{}^a$ is hydrogen or $C_{1-6}$ alkyl and $R_{20}$ is hydroxy, $C_{1-6}$ alkoxy, ar $C_{1-6}$ alkyloxy or —NHC(=A)NH_2 where A is oxygen or sulphur;

$R_7$ is nitro, cyano, halomethyl, heteroaryl, arylaminomethyl, ar $C_{1-6}$ alkylaminomethyl, $C_{1-6}$ alkylthio $C_{1-6}$ alkyl, arylthio $C_{1-6}$ alkyl, 1-H-tetrazol-5-yl, aryl $CH=NCH_2$—, or $CH_2NHC(=B)NHR_{17}$ where B is NCN, $NSO_2$Methyl, $NSO_2$Phenyl or $CHNO_2$;

or $R_7$ is the group $SO_2R_8$ in which $R_8$ is hydroxy, $C_{1-6}$ alkyl, aryl, or the group $NR_9R_{10}$ where $R_9$ and $R_{10}$ are the same or different and represent hydrogen, $C_{1-6}$ alkyl, aryl, or ar $C_{1-6}$ alkyl;

or $R_7$ is the group $COR_{11}$ where $R_{11}$ is hydrogen, hydroxy, $C_{1-6}$ alkoxy, aryloxy, ar $C_{1-6}$ alkyloxy, $C_{1-6}$ alkyl, aryl, ar $C_{1-6}$ alkyl or the group $NR_{12}R_{13}$ where $R_{12}$ is hydrogen or $C_{1-6}$ alkyl optionally substituted by a hydroxy or $C_{1-6}$ alkoxy group, and $R_{13}$ is hydrogen, $C_{1-6}$ alkyl (optionally substituted by a hydroxy or $C_{1-6}$ alkoxy group), $C_{3-6}$ alkenyl, aryl, ar $C_{1-6}$ alkyl, or $C_{3-8}$ cycloalkyl, or $NR_{12}R_{13}$ is pyrrolidino or piperidino, or $R_7$ is the group $CR_{11}{}^a=NR_{20}$ where $R_{11}{}^a$ is hydrogen, $C_{1-6}$ alkyl, aryl, or ar $C_{1-6}$ alkyl, and $R_{20}$ is as defined above;

or $R_7$ is the group $CH_2NR_{18}SO_2R_{14}$ where $R_{14}$ is $C_{1-6}$ alkyl or aryl, and $R_{18}$ is hydrogen or $C_{1-6}$ alkyl;

or $R_7$ is the group $CH_2NR_{18}COR_{15}$ where $R_{15}$ is hydrogen, $C_{1-6}$ alkyl, aryl, ar $C_{1-6}$ alkyl, $C_{1-6}$ alkoxy, halomethyl or the group $NHR_{16}$ where $R_{16}$ is hydrogen, $C_{1-6}$ alkyl, $C_{3-8}$ cycloalkyl, aryl, or ar $C_{1-6}$ alkyl, with the proviso that when the group $R_7$ contains a carbon atom through which it is linked to the alkylene group $(CH_2)_q$ then the total number of carbon atoms in the resulting chain is not greater than 6; and wherein:

the term aryl as a group or a part of a group means phenyl or a phenyl substituted with one or more $C_{1-3}$ alkyl or $C_{1-3}$ alkoxy groups or halogen atoms;

the term heteroaryl as a group or a part of a heteroaryl group means thienyl, pyridyl, furyl, pyrrolyl or thiazolyl which may be unsubstituted or substituted by a $C_{1-3}$ alkyl, $C_{1-3}$ alkoxy, hydroxy, hydroxy $C_{1-6}$ alkyl, amino $C_{1-6}$ alkyl, $C_{1-6}$ alkylamino $C_{1-6}$ alkyl, di $C_{1-6}$ alkylamino $C_{1-6}$ alkyl or halogen, the alkyl portion of the heteroaralkyl group is a straight or branched $C_{1-4}$ alkyl chain, and the heteroaryl ring is linked to the alkyl portion through either a carbon or nitrogen atom.

2. A compound as claimed in claim 1 in which $R_1$ represents $C_{1-12}$ alkyl, $C_{5-7}$ cycloalkyl, $C_{3-5}$ alkenyl, phenyl $C_{1-3}$ alkyl, $C_{1-4}$ alkyl substituted by a trifluoromethyl, hydroxy, $C_{1-3}$ alkoxy or di-$C_{1-3}$ alkylamino group or a heteraryl $C_{1-3}$ alkyl group where the heteroaryl ring contains one heteroatom; and $R_2$ represents hydrogen, methyl or ethyl; or $R_1R_2N$ represents a 5 to 8 membered ring optionally containing one double bond and/or substituted by one or two $C_{1-3}$ alkyl groups.

3. A compound as claimed in claim 1, wherein $R_4$ represents nitro, $C_{1-6}$ alkylthiomethyl, heteroarylmethyl where heteroaryl is thienyl, pyridyl, furyl, pyrrolyl or thiazolyl which may be unsubstituted or substituted by $C_{1-3}$ alkyl, $C_{1-3}$ alkoxy, hydroxy, hydroxy $C_{1-6}$ alkyl, amino $C_{1-6}$ alkyl, $C_{1-6}$ alkylamino $C_{1-6}$ alkyl, di $C_{1-6}$ alkylamino $C_{1-6}$ alkyl or halogen, the heteroaryl ring is linked to the methyl portion through either a carbon or nitrogen atom; $CH=NR_{20}$ where $R_{20}$ is hydroxy; or the group $(CH_2)_qR_7$ where q is zero, 1 or 2, and $R_7$ is the group $CH_2NHC(=B)NHR_{17}$ where B is NCN or $CHNO_2$ and $R_{17}$ is $C_{1-6}$ alkyl; or $R_7$ is the group $COR_{11}$ where $R_{11}$ is hydrogen, hydroxy or $NR_{12}R_{13}$ where $R_{12}$ and/or $R_{13}$ are hydrogen or $C_{1-6}$ alkyl or $NR_{12}R_{13}$ is pyrrolidino; or $R_7$ is the group $SO_2R_8$ where $R_8$ is $C_{1-6}$ alkyl or aryl; or $R_7$ is the group $CH_2NHSO_2R_{14}$ or $CH_2NHCOR_{15}$ where $R_{14}$ is $C_{1-6}$ alkyl, and $R_{15}$ is $C_{1-6}$ alkyl, aryl or $NHR_{16}$ where $R_{16}$ is aryl;

wherein the term aryl means phenyl or phenyl substituted by one or more $C_{1-3}$ alkyl or $C_{1-3}$ alkoxy groups or halogen atoms.

4. A compound as claimed in claim 1 in which $R_3$ represents hydrogen or $C_{1-3}$ alkyl.

5. A compound as claimed in claim 1 in which the group Alk is methylene.

6. A compound as claimed in claim 1 in which Q is a benzene ring incorporated through bonds at the 1- and 3-positions and the group $X(CH_2)_nY(CH_2)_m$ represents $—O(CH_2)_{3-5}—$ or $—O(CH_2)_2O(CH_2)_2—$.

7. A compound as claimed in claim 1 of the formula (IA)

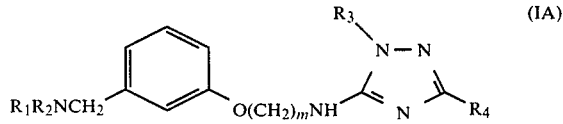

where $R_1R_2N$ is pyrrolidino, piperidino or hexamethylenimino; m is 3 or 4; $R_3$ is hydrogen or methyl; and $R_4$ is the group $(CH_2)_qR_7$ where q is zero, 1 or 2, and $R_7$ is methylthiomethyl, $CH_2NHC(=B)NHCH_3$ (where B is NCN or $CHNO_2$), $SO_2Me$, $CH=NOH$; or the group $COR_{11}$ where $R_{11}$ is hydroxy, amino, dimethylamino or pyrrolidino; or the group $CH_2NHSO_2Me$; or the group $CH_2NHCOR_{15}$ where $R_{15}$ is methyl or phenyl.

8. A compound which is
N-[[1-Methyl-5-[[3-[3-(1-piperidinylmethyl)phenoxy]propyl]amino]-1H-1,2,4-triazol-3-yl]methyl]methanesulphonamide and physiologically acceptable salts thereof.

9. A compound which is
1-Methyl-3-methylsulphonylmethyl-N-[3-[3-(1-piperidinylmethyl)phenoxy]propyl]-1H-1,2,4-triazole-5-amine and physiologically acceptable salts thereof.

10. A compound which is
N-[[1-Methyl-5-[[3-[3-(1-piperidinylmethyl)phenoxy]propyl]amino]-1H-1,2,4-triazol-3-yl]methyl]acetamide and physiologically acceptable salts thereof.

11. A compound which is
1-Methyl-5-[[3-[3-(1-piperidinylmethyl)phenoxy]propyl]amino]-1H-1,2,4-tiazole-3-carboxamide and physiologically acceptable salts thereof.

12. A compound as claimed in claim 1, in which $R_1$ represents hydrogen, $C_{1-10}$ alkyl, $C_{3-8}$ cycloalkyl, $C_{3-6}$ alkenyl, $C_{3-6}$ alkynyl, ar $C_{1-6}$ alkyl, trifluoro $C_{1-6}$ alkyl, or $C_{1-6}$ alkyl substituted by hydroxy, $C_{1-6}$ alkoxy, amino, $C_{1-6}$ alkylamino, di $C_{1-6}$ alkylamino or $C_{3-8}$ cycloalkyl; and $R_2$ represents hydrogen or $C_{1-4}$ alkyl; or $R_1$ and $R_2$ may together with the nitrogen atom to which they are attached form a pyrrolidino, piperidino, hexamethylenimino or tetrahydropyridino group which may be unsubstituted or may be substituted by one or more $C_{1-3}$ alkyl groups or a hydroxy group;

Alk represents a straight or branched alkylene chain of 1 to 6 carbon atoms;

Q represents a furan or thiophen ring in which incorporation into the rest of the molecule is through bonds at the 2- and 5-positions, the furan ring optionally bearing a further substituent $R_5$ adjacent to the group $R_1R_2N—Alk—$; or Q represents a benzene ring in which incorporation into the rest of the molecule is through bonds at the 1- and 3- or 1- and 4-positions;

$R_5$ represents halogen or $C_{1-4}$ alkyl which may be substituted by hydroxy or $C_{1-4}$ alkoxy;

X represents a bond, or when Q is a benzene ring and Y is methylene —NH—;

Y represents oxygen, sulphur or methylene;

n represents zero, 1 or 2;

m represents 2, 3 or 4;

$R_3$ represents hydrogen, $C_{1-6}$ alkyl, $C_{3-6}$ alkenyl, ar $C_{1-6}$ alkyl, or $C_{2-6}$ alkyl substituted by hydroxy or $C_{1-6}$ alkoxy; and $R_4$ represents the group $(CH_2)_qR_7$ where q is zero, 1, 2, 3, 4, 5 or 6 and the alkylene chain $(CH_2)_q$ may be straight or branched, and $R_7$ is nitro, cyano, halomethyl, heteroaryl which is thienyl, pyridyl, furyl, pyrrolyl or thiazolyl which may be unsubstituted or substituted by $C_{1-3}$ alkyl, $C_{1-3}$ alkoxy, hydroxy, hydroxy $C_{1-6}$ alkyl, amino $C_{1-6}$ alkyl, $C_{1-6}$ alkylamino $C_{1-6}$ alkyl, di $C_{1-6}$ alkylamino $C_{1-6}$ alkyl or halogen; arylaminomethyl, ar $C_{1-6}$ alkylaminomethyl, or aryl $CH=NCH_2—$;

or $R_7$ is the group $SO_2R_8$ in which $R_8$ is $C_{1-6}$ alkyl or the group $NR_9R_{10}$ where $R_9$ and $R_{10}$ are the same or different and represent hydrogen, $C_{1-6}$ alkyl, aryl, or ar $C_{1-6}$ alkyl;

or $R_7$ is the group $COR_{11}$ where $R_{11}$ is hydrogen, hydroxy, $C_{1-6}$ alkoxy, aryloxy, ar $C_{1-6}$ alkyloxy, $C_{1-6}$ alkyl, aryl, ar $C_{1-6}$ alkyl, or the group $NR_{12}R_{13}$ where $R_{12}$ is a hydrogen or $C_{1-6}$ alkyl optionally substituted by a hydroxy or $C_{1-6}$ alkoxy group, and $R_{13}$ is hydrogen, $C_{1-6}$ alkyl optionally substituted by a hydroxy or $C_{1-6}$ alkoxy group, $C_{3-6}$ alkenyl, aryl, ar $C_{1-6}$ alkyl, or $C_{3-8}$ cycloalkyl, or $NR_{12}R_{13}$ is pyrrolidino which may be substituted by hydroxy or one or two $C_{1-3}$ alkyl groups;

or $R_7$ is the group $CR_{11}{}^a=NR_{20}$ where $R_{11}{}^a$ is hydrogen, $C_{1-6}$ alkyl, aryl, or ar $C_{1-6}$ alkyl, and $R_{20}$ is hydroxy, $C_{1-6}$ alkoxy or $—NHC(=A)NH_2$ where A is oxygen or sulphur;

or $R_7$ is the group $CH_2NR_{18}SO_2R_{14}$ where $R_{14}$ is $C_{1-6}$ alkyl or aryl, and $R_{18}$ is hydrogen or $C_{1-6}$ alkyl;

or $R_7$ is the group $CH_2NR_{18}COR_{15}$ where $R_{15}$ is hydrogen, $C_{1-6}$ alkyl, aryl, ar $C_{1-6}$ alkyl, $C_{1-6}$ alkoxy or the group $NHR_{16}$ where $R_{16}$ is hydrogen, $C_{1-6}$ alkyl, $C_{3-8}$ cycloalkyl, aryl, or ar $C_{1-6}$ alkyl; with the proviso that when the group $R_7$ contains a carbon atom through which it is linked to the alkylene group $(CH_2)_q$ then the total number of carbon atoms in the resulting chain is not greater than 6; and wherein the term aryl as a group or part of a group means phenyl or phenyl substituted by one or more $C_{1-3}$ alkyl or $C_{1-3}$ alkoxy groups or halogen atoms.

13. A pharmaceutical composition for the treatment of conditions mediated through $H_2$-receptors comprising an effective amount of at least one compound as claimed in claim 1 together with at least one pharmaceutically acceptable carrier or diluent.

14. A method of treating a condition mediated through histamine $H_2$-receptors which comprises administering to a patient an effective amount of a compound according to claim 1 to relieve said condition.

15. A pharmaceutical composition for the treatment of conditions mediated through $H_2$-receptors comprising an effective amount of a compound as claimed in claim 9 together with at least one pharmaceutically acceptable carrier or diluent.

16. A method of treating a condition mediated through histamine $H_2$-receptors which comprises administering to a patient an effective amount of a compound according to claim 9 to relieve said condition.

17. A compound as claimed in claim 1 of the formula

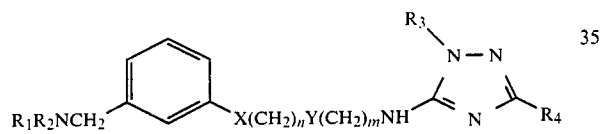

where $R_1$ represents $C_{1-12}$alkyl, $C_{5-7}$cycloalkyl, $C_{3-5}$alkenyl, phenyl $C_{1-3}$alkyl, $C_{1-4}$alkyl substituted by a trifluoromethyl, hydroxy, $C_{1-3}$alkoxy or di-$C_{1-3}$alkylamino group, or a heteroaryl $C_{1-3}$alkyl group where the heteroaryl ring is thienyl, pyridyl, furyl, pyrrolyl, 5-methylfuran-2-yl or 5-hydroxymethylfuran-2-yl; and $R_2$ represents hydrogen, methyl or ethyl; or $R_1R_2N$ represents a pyrrolidino, piperidino, hexamethylenimino, tetrahydropyridino, 4-hydroxypiperidino, or a 4-methylpiperidino ring;

the group $X(CH_2)_nY(CH_2)_m$ represents $-O(CH_2)_{3-5}-$ or $-O(CH_2)_2O(CH_2)_2-$; $R_3$ represents hydrogen or $C_{1-3}$alkyl; and $R_4$ represents nitro, $C_{1-6}$alkylthiomethyl, heteroarylmethyl (where heteroaryl is thienyl, pyridyl, furyl, pyrrolyl or thiazolyl which may be unsubstituted or substituted by $C_{1-3}$alkyl, $C_{1-3}$alkoxy, hydroxy, hydroxy $C_{1-6}$alkyl, amino $C_{1-6}$alkyl, $C_{1-6}$alkylamino $C_{1-6}$alkyl, di$C_{1-6}$alkylamino $C_{1-6}$alkyl or halogen, and the heteroaryl ring is linked to the methyl portion through either a carbon or nitrogen atom), $CH=NR_{20}$ where $R_{20}$ is hydroxy; or $R_4$ represents the group $(CH_2)_qR_7$ where q is zero, 1 or 2, and $R_7$ is the group $CH_2NHC(=B)NHR_{17}$ where B is NCN or $CHNO_2$ and $R_{17}$ is $C_{1-6}$alkyl, or $R_7$ is the group $COR_{11}$ where $R_{11}$ is hydrogen, hydroxy or $NR_{12}R_{13}$ where $R_{12}$ and/or $R_{13}$ are hydrogen or $C_{1-6}$alkyl or $NR_{12}R_{13}$ is pyrrolidino, or $R_7$ is the group $SO_2R_8$ where $R_8$ is $C_{1-6}$alkyl or aryl, or $R_7$ is the group $CH_2NHSO_2R_{14}$ or $CH_2NHCOR_{15}$ where $R_{14}$ is $C_{1-6}$alkyl, and $R_{15}$ is $C_{1-6}$alkyl, aryl, or $NHR_{16}$ where $R_{16}$ is aryl, and wherein the term aryl means phenyl or phenyl substituted by one or more $C_{1-3}$ alkyl or $C_{1-3}$ alkoxy groups or halogen atoms.

18. A compound as claimed in claim 1 of the formula:

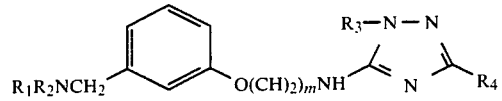

where $R_1R_2N$ is pyrrolidino, piperidino or hexamethylenimino; m is 3 or 4; $R_3$ is hydrogen or methyl; and $R_4$ is the group $(CH_2)_qR_7$ where q is zero, 1 or 2, $R_7$ is $SO_2R_8$ and $R_8$ is $C_{1-4}$ alkyl.

19. A pharmaceutical composition according to claim 15 in a form adapted for oral or parenteral administration.

* * * * *